(12) United States Patent
Strocchia-Rivera

(10) Patent No.: US 6,462,817 B1
(45) Date of Patent: Oct. 8, 2002

(54) METHOD OF MONITORING ION IMPLANTS BY EXAMINATION OF AN OVERLYING MASKING MATERIAL

(76) Inventor: Carlos Strocchia-Rivera, 15 Dogwood Knolls, Highland, NY (US) 12528

( * ) Notice: Subject to any disclaimer, the term of this patent is extended or adjusted under 35 U.S.C. 154(b) by 0 days.

(21) Appl. No.: 09/570,135

(22) Filed: May 12, 2000

(51) Int. Cl.$^7$ .................................................. G01J 4/00
(52) U.S. Cl. ...................................................... 356/369
(58) Field of Search ................................. 356/369, 364, 356/367, 368, 381, 382, 72, 73, 351, 355; 250/225

(56) References Cited

U.S. PATENT DOCUMENTS

| | | |
|---|---|---|
| 4,352,016 A | 9/1982 | Duffy et al. |
| 4,352,017 A | 9/1982 | Duffy et al. |
| 4,511,800 A | 4/1985 | Harbeke et al. |
| 4,766,317 A | 8/1988 | Harbeke et al. |
| 4,770,536 A | 9/1988 | Golberstein |
| 4,807,994 A * | 2/1989 | Felch et al. .................. 356/326 |
| 4,899,055 A | 2/1990 | Adams et al. |
| 4,905,170 A | 2/1990 | Forouhi et al. |
| 4,966,457 A | 10/1990 | Hayano et al. |
| 4,999,014 A | 3/1991 | Gold et al. |
| 5,042,951 A | 8/1991 | Gold et al. |
| 5,074,669 A | 12/1991 | Opsal |
| 5,412,473 A | 5/1995 | Rosencwaig et al. |
| 5,517,312 A | 5/1996 | Finarov |
| 5,520,769 A | 5/1996 | Barrett et al. |
| 5,581,350 A | 12/1996 | Chen et al. |
| 5,596,406 A | 1/1997 | Rosencwaig et al. |
| 5,596,411 A | 1/1997 | Fanton et al. |
| 5,608,526 A | 3/1997 | Piwonka-Corle et al. |
| 5,747,813 A | 5/1998 | Norton et al. |
| 5,764,365 A | 6/1998 | Finarov |
| 5,771,094 A | 6/1998 | Carter et al. |
| 5,798,837 A | 8/1998 | Aspnes et al. |
| 5,859,424 A | 1/1999 | Norton et al. |
| 5,877,859 A | 3/1999 | Aspnes et al. |
| 5,889,593 A | 3/1999 | Bareket |
| 5,900,939 A | 5/1999 | Aspnes et al. |
| 5,910,842 A | 6/1999 | Piwonka-Corle et al. |
| 5,917,594 A | 6/1999 | Norton |
| 5,973,787 A | 10/1999 | Aspnes et al. |
| 5,978,074 A | 11/1999 | Opsal et al. |
| 6,052,185 A * | 4/2000 | Banet et al. .................. 356/345 |
| 6,141,103 A * | 10/2000 | Pinaton et al. .............. 356/369 |
| 6,211,961 B1 * | 4/2001 | Maris ........................ 356/432 |

FOREIGN PATENT DOCUMENTS

| | | |
|---|---|---|
| WO | 99/02970 | 1/1999 |
| WO | 99/45340 | 10/1999 |
| WO | 99/59182 | 11/1999 |
| WO | 00/02229 | 1/2000 |

OTHER PUBLICATIONS

International Search Report, application No. PCT/US 01/15281, mailed Nov. 16, 2001.

* cited by examiner

*Primary Examiner*—Michael P. Stafira
(74) *Attorney, Agent, or Firm*—Eric B. Meyertons; Ann Marie Mewherter; Conley, Rose & Tayon P.C.

(57) ABSTRACT

A process control method to monitor ion implantation process conditions by measuring the optical properties of a masking material is provided. A patterned masking material may protect underlying regions of a semiconductor substrate from undergoing a chemical or physical change during an ion implantation process. The patterned masking material, however, may also undergo a chemical or physical change during processing. The chemical or physical changes to the masking material during such processing may also cause the optical properties of the material to change. The optical properties of the masking material may be used to determine the concentration of ions implanted into the semiconductor substrate.

70 Claims, 9 Drawing Sheets

METHOD OF MONITORING ION IMPLANTS BY EXAMINATION OF AN OVERLYING MASKING MATERIAL

BACKGROUND OF THE INVENTION

1. Field of the Invention

This invention generally relates to an ion implantation process. Certain embodiments relate to monitoring and/or evaluating an ion implantation process by measuring the optical properties of a wafer during processing.

2. Description of the Related Art

Ion implantation is typically used to introduce impurity materials, or dopant ions, into the surface of a semiconductor device. Because ion implantation offers several advantages over diffusion doping, it is becoming an integral part of many semiconductor fabrication processes. Ion implanters, however, are among the most sophisticated and complex systems in semiconductor manufacturing. In order to be utilized efficiently, ion implanters may require frequent monitoring and careful operation. For example, ion implantation systems may introduce a number of defects (e.g., non-uniformities) into the semiconductor process. Such defects may cause significant yield problems. A defect may result from contamination, such as material that is sputtered from the semiconductor substrate or wafer surface as a result of ion bombardment. The accumulation of contaminants over time may adversely affect the performance of the ion implanter and may reduce the wafer yield below acceptable levels.

In order to take advantage of the benefits of ion implantation processes, extensive characterization is typically performed to ensure that the process is within design tolerance. Ideally, extensive characterization of the process takes place both during process development and during process control of manufacturing processes. Typically, ion implantation processes are characterized by implant dose, uniformity of implant dose across the wafer, uniformity of dose across several wafers, and implantation depth profiles. Accurate measurement of the implant dose, however, may be a difficult task because the measurement is generally based on integrating the beam current. Error sources may be introduced into the measurement of the integrated beam current by interactions between the beam and electrons, neutrals, and negative ions as well as secondary particles which may be emitted as a result of ion bombardment of the target.

One process control method that may be used to monitor and assess an ion implantation process involves determining the sheet resistance of implanted wafers using a four-point probe technique. The four-point probe technique involves using a colinear probe arrangement which is arranged to contact the implanted regions on the semiconductor wafer. In operation, a current is passed between the two outer probes and the voltage drop across the two inner probes is measured. The test is typically performed twice in order to eliminate thermoelectric heating and cooling errors from the measurements. The first test involves passing a current in a first direction, referred to as the forward direction. The second test then involves passing the current in a second direction, opposite to the first direction, referred to as the reverse direction. The two voltage readings may then be averaged. The test may also be performed at several different current levels because testing at an improper current may cause the forward and reverse test results to differ or to cause the readings to drift.

Because the impurity regions must be electrically activated prior to electrical testing, this process control method may introduce several additional processing steps to the fabrication of a monitor or test wafer. For example, the impurity regions are typically electrically activated by rapid thermal processing. During this processing, masking materials such as photoresist may volatilize or reflow which may cause contamination or removal problems in subsequent processing. Therefore, the photoresist or other masking material is typically removed prior to electrically activating the impurity regions. Consequently, the time required to perform these additional processing steps increases the processing time and cost associated with electrical testing. Furthermore, long test times may be extremely costly if additional wafers have been processed incorrectly before the electrical test results were available. Suspending processing until the electrical test results are available, however, may also be costly due to production delays and idle production tools.

Optical dosimetry may also be used to monitor and control ion implantation processes. This technique measures the darkening, or increased optical absorption, of photoresist that occurs due to exposure to ion beams. Monitor wafers may be prepared by coating photoresist onto a transparent substrate. The monitor wafer is then scanned with a dosimeter to determine its background optical absorption. The wafer may then be subjected to an ion implantation process. After implantation, the wafer may be scanned again using the dosimeter, and the background optical absorption may be subtracted from this data. In this manner, the distribution of implanted ions across the entire wafer may be measured and plotted on a contour plot. From the plot of this data, variations and trends in the distribution of implanted ions across the wafer may be discerned. Additionally, the extent of the variations and trends may be analyzed to determine if the ion implantation process is within design tolerances.

Optical dosimetry may be particularly useful when making qualitative assessments of the performance of an ion implantation process. In addition, this technique allows the diagnosis of an ion implantation step to be done with greater resolution and sensitivity. For example, scan lock-up, non-linear scanning, and loss of beam diameter control may be detected using the optical dosimetry technique. Scan lock-up is a common problem which may result from overlap of individual Gaussian beam traces and may cause dopant non-uniformities across the wafer. Scan lock-up may be particularly problematic at low dopant doses. For example, low dopant doses typically have decreased beam currents and scan times which may lead to significant overlap in some regions of the wafer and doping level gaps in other regions of the wafer. Non-linear scanning may result from beam neutralization caused by collisions between ions and residual gas atoms in the beam chamber and neutralization from thermal electrons caught in the beam. Positive charge build-up on an insulating layer on the wafer may also result in non-linear scanning because the build-up may alter the charge balance in the ion beam and lead to significant dose variations across the wafer. Loss of beam diameter control, or defocusing, is another common problem in ion implantation which may result from separation of the beam due to repulsion of like charges. Defocusing of the beam may also cause uneven ion density and non-uniform implant concentrations in the wafer.

There are several disadvantages, however, in using the optical dosimetry technique to monitor ion implantation processes. For example, because only a photoresist-coated transparent substrate may be used in this technique, additional processing steps and materials are typically required. Furthermore, the testing method may not accurately predict the ion implantation performance of a product wafer which may have a topography which differs dramatically from a substrate coated with a planar resist layer. For example, positive charge build-up on a wafer may be particularly problematic when implanting into an insulating layer, such as resist or silicon dioxide, which may lead to significant dose variations across the wafer. The topography or patterning of the masking layer on a product wafer may cause additional localized positive charge build-up. A wafer having a planar resist layer may not accurately show the localization of positive charge build-up. Therefore, using a dissimilar test wafer may not accurately detect all of the potential problems that may occur in an ion implantation process.

Another process control method which may be used to monitor and control ion implantation processes involves the use of modulated and non-modulated reflectance. An example of such a process control method and apparatus is illustrated in U.S. Pat. No. 5,074,669 to Opsal which is incorporated by reference as if fully set forth herein. A modulated signal may be obtained by periodically exciting a semiconductor substrate with a focused, intensity modulated, pump laser beam. The reflected power of the probe is measured to yield a first modulated reflectance signal. A second measurement is taken of the non-modulated reflectance signal using the argon laser in a non-modulated operating configuration. In addition, a third measurement is also taken of a non-modulated reflectance signal using a second laser beam in a non-modulated operating configuration. These three measurements may be correlated with the dosage level. The three reflectance measurements, therefore, provide three independent measurements. This data may then be used in conjunction with a mathematical model to characterize an ion implantation process.

There are several disadvantages, however, to using the modulated and non-modulated reflectance technique as a process control method for ion implantation. For example, certain films will exhibit a great sensitivity, or signal response, to certain wavelengths. In the above example, therefore, if a masking layer is chosen that is substantially different than silicon dioxide, it may be necessary to change the lasers that are used in the system. Measurements at single wavelengths may also inherently have more ambiguities than multiple wavelength measurements. Therefore, this approach may not be particularly useful when the index of refraction of the material is not accurately known. Furthermore, the number of layers which may be analyzed using this method is proportional to the number of independent measurements that are taken. Analysis of complex multi-layer stacks, therefore, would necessitate performing additional measurements. Using single-wavelength sources and analyzing multi-layer stacks may require incorporating additional lasers into the system.

Alternative nondestructive optical testing, such as spectroscopic ellipsometry and spectroscopic reflectometry, is becoming increasingly popular to characterize semiconductor films. In these techniques, electromagnetic radiation may be impinged upon a sample, and the reflected radiation may be measured. Reflectance data may then be used to determine characteristics of the semiconductor films such as the thickness of a single or multiple layer or the refractive index. Many different materials may be characterized using reflectance data including, for example, photoresist, silicon oxide, silicon nitride, titanium nitride and polysilicon. Spectroscopic ellipsometry involves impinging an incident radiation beam having a known polarization state on the sample and measuring the polarization of the reflected radiation. Spectroscopic reflectometry involves impinging an incident radiation beam on the sample and measuring the intensity of the reflected radiation. The incident radiation, in both techniques, may include multiple frequency components which provide reflectance data for at least two frequency components. Examples of spectroscopic reflectometers and ellipsometers are illustrated in U.S. Pat. No. 4,999,014 to Gold et al., U.S. Pat. No. 5,042,951 to Gold et al., U.S. Pat. No. 5,412,473 to Rosencwaig et al., U.S. Pat. No. 5,581,350 to Chen et al., U.S. Pat. No. 5,596,406 to Rosencwaig et al., U.S. Pat. No. 5,596,411 to Fanton et al., U.S. Pat. No. 5,747,813 to Norton et al., 5,771,094 to Carter et al., U.S. Pat. No. 5,798,837 to Aspnes et al., U.S. Pat. No. 5,877,859 to Aspnes et al., U.S. Pat. No. 5,889,593 to Bareket et al., U.S. Pat. No. 5,900,939 to Aspnes et al., U.S. Pat. No. 5,917,594 to Norton and U.S. Pat. No. 5,973,787 to Aspnes et al., all of which are incorporated by reference as if fully set forth herein. Additional examples of spectroscopic devices are illustrated in PCT Application No. WO 99/02970 to Rosencwaig et al. and is incorporated by reference as if fully set forth herein.

Recent advances in spectroscopic ellipsometers and spectrophotometers have provided an incident radiation beam having a reduced spot size. As such, a very small region of the semiconductor film may be analyzed using these techniques. In this respect, a single feature of a semiconductor device, such as a masking layer over the gate conductor of a single transistor, may be characterized using these methods. Examples of focused beam spectroscopic ellipsometry and reflectometry methods and systems are illustrated in U.S. Pat. No. 5,608,526 to Piwonka-Corle et al., U.S. Pat. No. 5,859,424 to Norton et al., and U.S. Pat. No. 5,910,842 to Piwonka-Corle et al., all of which are incorporated by reference as if fully set forth herein.

Accordingly, it would be advantageous to develop a nondestructive optical testing method to rapidly and accurately measure, assess, and monitor an ion implantation process without sacrificing product wafers or processing additional monitor wafers.

SUMMARY OF THE INVENTION

An embodiment of the invention relates to a method to evaluate an ion implantation process. A masking material may be formed on a semiconductor substrate. Any material that is substantially transparent to a portion of the light produced by an optical inspection device may be used as a masking material. In addition, the masking material may substantially inhibit implantation of dopant ions into the underlying semiconductor substrate. Alternatively, the dopant ions may be implanted into a semiconductor substrate through the masking material. Implanting the dopant ions through a masking material may enhance the distribution profile of the implanted region by randomizing the directional paths of the ions which are being driven into the semiconductor substrate. Appropriate masking materials may include, but are not limited to, a resist material, silicon dioxide, silicon nitride, titanium nitride, or polycrystalline silicon. A masking material may also include several layers of different materials such as a resist material disposed upon an inorganic material. An appropriate masking material may be determined by the semiconductor device feature which may be formed by an ion implantation process. As such, an appropriate masking material may also be determined by the ion implantation process conditions being used to fabricate the semiconductor device such as dopant species or implant energy.

The implantation of ions into the masking material may cause physical damage and chemical changes in the masking material. For example, an implanted masking material may include an upper portion which includes a physically damaged layer of the masking material. The ions which have been implanted into the masking material may be substantially disposed in a middle portion of the masking material. A lower portion of the masking material may be substantially free of implanted ions. Therefore, the implantation of ions into the masking material may also alter an optical property of the masking material. An optical property of the masking material may be measured using a broadband radiation technique. Broadband radiation techniques which may be used to measure the optical property include, but are not limited to, spectroscopic ellipsometry and spectroscopic reflectometry. Optical properties of the masking material may include a thickness of a portion of the masking material, a thickness of the entire masking material, an index of refraction, or an extinction coefficient.

In an embodiment, a characteristic of the implanted ions in the masking material may be determined. The characteristic may be a function of the measured optical property of the implanted masking material. Characteristics of the implanted ions in the masking material which may be determined include, but are not limited to, an implantation energy when the ions are implanted into the masking material, a species of the implanted ions, and a concentration of the implanted ions. The presence of implanted ions in the masking material may also be determined using the measured optical property of the implanted masking material. In an embodiment, the measured optical property of the masking material may also be used to determine a characteristic of an implanted portion of a semiconductor substrate. A characteristic of an implanted portion of a semiconductor substrate may also be a function of the measured optical property of the masking material. Characteristics of the implanted ions in a portion of the semiconductor substrate include, but are not limited to, an implantation energy and a dose of the implanted ions when the ions are implanted into a portion of the semiconductor substrate. Additional characteristics which may be determined using a measured optical property of the masking material may include a concentration, a presence, a depth, and a distribution of the implanted ions in the portion of the semiconductor substrate.

In an additional embodiment, ions may also be implanted into a portion of a semiconductor substrate. Implantation of ions into a semiconductor substrate may be performed by implanting ions through a masking material. Alternatively, at least a portion of a masking material may be removed to expose a portion of a semiconductor substrate. A semiconductor substrate may also experience significant damage due to the implantation of ions into regions of the semiconductor substrate. For example, damage to the silicon by the implanted ions may produce an amorphous layer below an upper crystalline damaged layer. As such, implantation of ions into a portion of a semiconductor may alter an optical property of the semiconductor substrate. Therefore, an optical property of an implanted portion of a semiconductor substrate may be measured and used to determine a characteristic of implanted ions in a portion of a semiconductor substrate. The characteristic of the implanted ions in a portion of a semiconductor substrate may, therefore, be a function of the measured optical property of the implanted portion of the semiconductor substrate. Optical properties of the implanted portion of the semiconductor substrates may include a thickness, an index of refraction, or an extinction coefficient. The characteristic may include any of the characteristics which are described in an above embodiment. In an embodiment, a method to fabricate a semiconductor device may include implanting ions into a wafer, measuring an optical property of the wafer, and determining at least one characteristic of the implanted ions in the wafer. The wafer may include a masking material arranged upon a semiconductor substrate.

In an embodiment, a reference wafer may be formed by implanting ions into a first masking material which may be formed on at least a portion of a first semiconductor substrate using first ion implantation conditions. A product wafer may also be formed by implanting ions into a second masking material which may be arranged over at least a portion of a second semiconductor substrate using second ion implantation conditions. The first and second masking materials formed on the semiconductor substrates may be substantially identical. In addition, the first and second semiconductor substrates may also be substantially identical. The first and second ion implantation conditions may include, but are not limited to, process conditions such as dopant species, a dopant dose, an ion energy, and angle of implantation, and/or a temperature of the implantation process. Parameters of an instrument used to produce the first ion implantation conditions may be substantially similar to parameters of the instrument used to produce the second ion implantation conditions. Alternatively, at least one parameter of an instrument used to produce the second ion implantation conditions may be substantially different than a parameter of an instrument used to produce the first ion implantation conditions.

An optical property of the first and second implanted masking materials may be measured using a broadband radiation technique. The measured optical properties of the first and second masking material may also be compared. As such, comparison of the optical properties of the first and second masking materials may be used to determine if the first and second ion implantation conditions produced by parameters of the instrument are substantially the same. In this manner, a quantitative relationship which describes a relationship between the measured optical properties of the first and second masking materials and the parameters of the instruments used to produce the first and second ion implantation conditions may also be determined. In an additional embodiment, ions may also be implanted into at least a portion of the first and second semiconductor substrates. Therefore, an optical property of the first and second implanted masking materials may also be measured using a broadband radiation technique. Comparison of the optical properties of the first and second semiconductor substrates may also be used to determine if the first and second ion implantation conditions produced by the parameters of the instrument are substantially similar. Furthermore, comparison of the optical properties of the first and second implanted portions of the semiconductor substrates may be used to determine a quantitative relationship between the optical properties of the implanted semiconductor substrate and the ion implantation conditions.

In a further embodiment, a computer-controlled method may be used to control an optical inspection, or spectroscopic, device. The optical inspection device may be used to measure an optical property of an ion implanted masking material. The computer-controlled method may include measuring the optical property by using an optical model to calculate the optical property of the masking material. As such, the computer-controlled method may also be used to determine an appropriate optical model to calculate the optical property. Appropriate optical models may include, but are not limited to, a cauchy model, a harmonic oscillator model, and a polynomial series expansion model.

The computer-controlled method may also include determining at least one characteristic of the implanted ions in the masking material. In an additional embodiment, the method may include generating a set of data. The set of data may include measured optical properties of a masking material and determined characteristics of implanted ions in the masking material. The set of data may also include data which may be generated by using different devices which may be configured to measure optical properties and to determined a characteristic of the implanted ions. As such, the set of data may be used to calibrate or monitor the performance of additional devices. In an additional embodiment, a system may include an optical inspection device, a controller computer coupled to the device, and controller software executable on the controller computer. The controller software may be operable to implement the computer-controlled method to control the optical inspection device. In an embodiment, the computer-controlled method may be implemented by program instructions which may be computer-executable and may be incorporated into a carrier medium.

In an additional embodiment, a system may include an ion implanter and a spectroscopic device. The ion implanter may be used to produce and direct ions toward a wafer. The wafer may include a masking material arranged upon a semiconductor substrate. The spectroscopic device may be coupled to the ion implanter and may be used to measure an optical property of an implanted masking material or an implanted semiconductor substrate. The system may also be used to measure variations in an optical property of the masking material or the semiconductor substrate during implantation of ions into the wafer. Therefore, the system may also be used to generate a signature which may characterize the implantation of ions into the wafer. The signature may also include at least one singularity which may be representative of an end of implantation. As such, the system may be used to determine an endpoint of the implantation process.

In a further embodiment, a system may include a spectroscopic device, an operating system, and a dual-beam device. The spectroscopic device may be configured to measure an optical property of a wafer. The wafer may include a masking material arranged on a semiconductor substrate. In addition, the operating system may be coupled to the spectroscopic device and the dual-beam device and may be used to determine a characteristic of the implanted ions in the wafer. The operating system may also include a controller computer and controller software executable on the controller computer. The controller software may also be operable to implement a method to control the spectroscopic device and to control the dual-beam device. Additionally, the dual-beam device may be used to directly measure a thickness of the masking material arranged on the semiconductor substrate.

BRIEF DESCRIPTION OF THE DRAWINGS

Other objects and advantages of the invention will become apparent upon reading the following detailed description and upon reference to the accompanying drawings in which.

Figure 1:
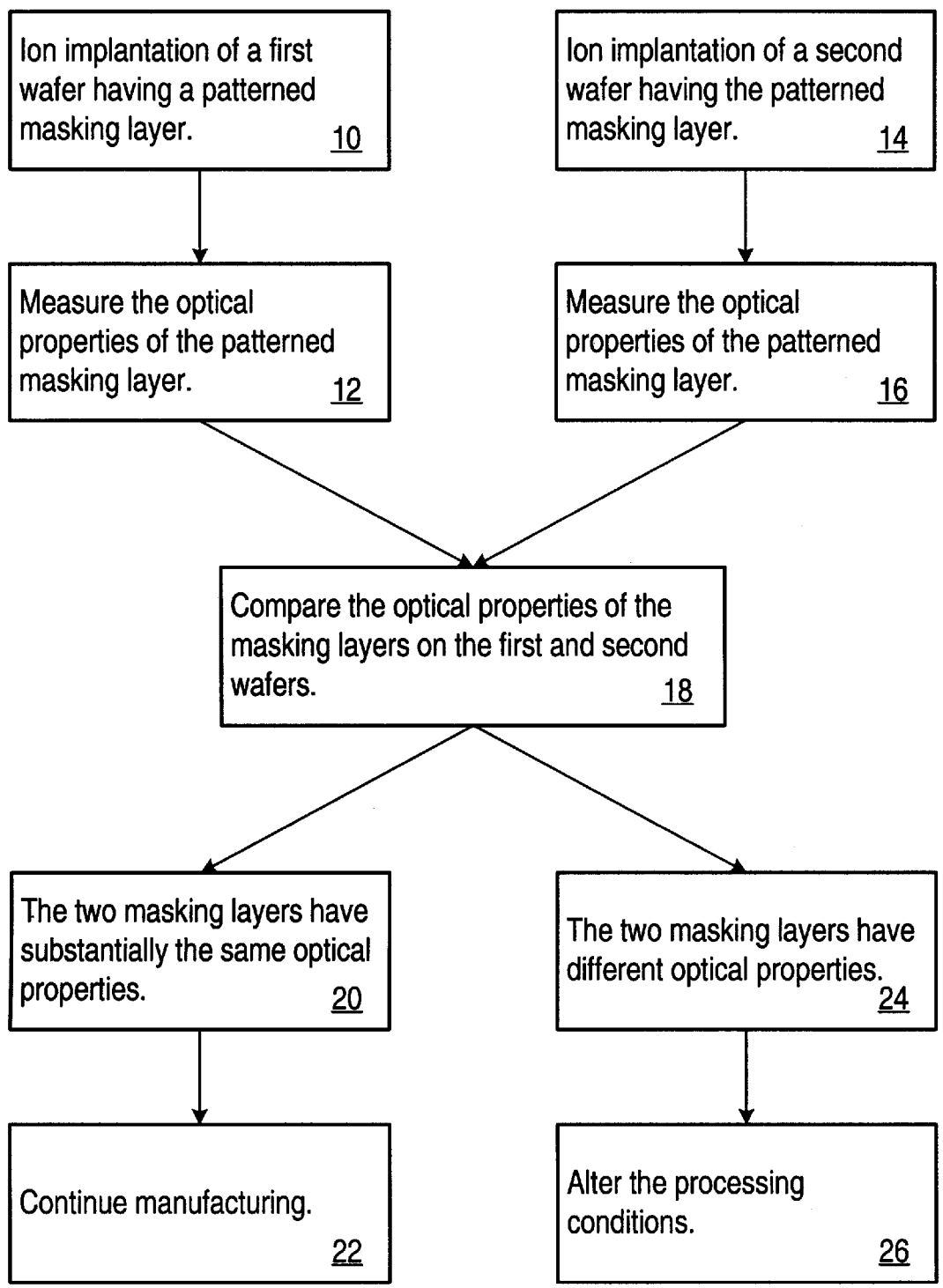
FIG. 1 depicts a flow chart illustrating a process control method to monitor and adjust an ion implantation process using spectroscopic ellipsometry or reflectometry to analyze an optical property of a masking layer.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

An ion implantation process typically involves the implantation of ions into a semiconductor substrate. A semiconductor substrate, in one embodiment, may be a silicon wafer. Alternatively, a semiconductor substrate may be a silicon wafer which includes a number of devices (e.g., transistors) formed upon the upper surface of the silicon wafer. The implantation of ions into a semiconductor substrate may be performed to alter the electronic properties of the semiconductor substrate. The electrical properties of the implanted semiconductor substrate typically depend on the concentration of ions implanted into the semiconductor substrate. The electrical properties of the implanted semiconductor substrate may also depend on the depth of the implanted portion of the semiconductor substrate, and the distribution of the implanted ions as a function of thickness of the implanted portion of the semiconductor substrate. The implanted ion characteristics of the implanted semiconductor substrate may typically depend on a number of factors, including, but not limited to, the identity of the ions, the implantation energy, the implantation dose, and the masking materials used during the process. For many semiconductor manufacturing applications it is important to be able to accurately determine the implant characteristics after performing an ion implantation process.

In an embodiment, ions may be implanted into a masking material formed on a semiconductor substrate. During an ion implantation process, ions will enter the masking material and alter the physical and/or chemical properties of the masking material. Chemical changes and physical damage to the masking material may occur due to incorporation of the dopant ions. Additionally, the extent of the chemical change in the masking material may vary depending on the processing conditions that are used during the ion implantation. For example, the upper portion of the masking material may undergo physical damage due to the collisions of the high energy ions with the upper surface of the masking material. The masking material may also be implanted with dopant ions to some extent during an ion implantation process. Underneath the damaged upper portion of the masking layer, therefore, a middle portion may exist in which the ions that do not pass through the masking layer will reside. Beneath the middle portion, a lower portion may exist which is substantially unaltered by the ion implantation process. The lower portion may extend to the upper surface of the underlying semiconductor substrate. The chemical and physical changes in the masking material due to ion implantation may cause changes in an optical property of the masking material. After ion implantation, therefore, at least one optical property of the masking material may be measured and used to determine characteristics of the implantation of ions into the masking material or characteristics of the implanted region resulting from the ion implantation process. Characteristics of the implantation of ions into the masking material may include, but are not limited to, implant energy, ion species, implant dose, and a presence of implanted ions in the masking material. Characteristics of the implanted region of the semiconductor substrate resulting from the ion implantation process may include, but are not limited to, implant energy, ion species, impant dose, concentration of ions, a depth of the implanted region, a presence of implanted ions in the semiconductor substrate, and a distribution of implanted ions as a function of thickness of the implanted region.

In some embodiments, an optical property of the upper, middle, or lower portion of the masking material may be used to determine a characteristic of the implanted ions in the masking material, such as the energy of the ion implantation process. During an ion implantation process, ions may be driven into the masking material. The implantation of ions into the masking material may cause physical damage to the upper surface of the masking material and may reside in the middle portion of the masking material. The depth to which the ions cause damage to the upper portion of the masking material may be a function of the energy of the ions. Similarly, the depth to which the ions are driven within the masking material may also be a function of the energy of the ions. Higher energy implantation processes may cause more damage to an upper portion of the masking material and drive the ions farther into the masking material than low energy ion implantation process. Therefore, the depth of the upper and middle portions of the masking material may be related to the implant energy of the ion implantation process. The depth of the upper and middle portions of the masking material may also be related to other process conditions of the ion implantation such as the species of ions being implanted or the implant dose. In addition, the measured thickness of the lower portion of the masking material may also be associated with a specific ion implantation energy. The thickness of the upper, middle, and lower portions may be determined by measuring an optical property of the masking material. The implantation of ions into the masking material or the implanted masking material resulting from the ion implantation process may, therefore, be determined as a function of the measured optical property of the masking material.

In additional embodiments, an implanted masking material may be analyzed as a single substantially homogenous layer. Therefore, an optical property of an entire implanted masking material may also be measured. The entire implanted masking material may include a combination of upper, middle, and lower portions of the implanted masking material. The individual optical properties of the upper, middle, and lower portions may, therefore, be effectively included in the measurement of the optical property of the entire implanted masking material. For example, an optical property of the entire implanted masking layer may include the added or averaged optical properties of the individual layers. Measuring an optical property of the masking material as a single layer may then be used to determine the ion implantation conditions. In one example, an optical property of the entire thickness of the masking material may be compared to an optical property of the masking material prior to ion implantation. Therefore, the comparison of the optical properties may indicate a change in the optical property of the masking material subsequent to the ion implantation. A change in the optical property of the masking material may be attributed to implanted ions which may be present in the masking material. In addition, an optical property of the entire implanted masking material may also be compared to a reference optical property of the entire masking material which was implanted using known conditions. In this manner, comparing the optical properties of the two implanted masking materials may indicate if the ion implantation process is producing substantially the same implantation of ions over time or across several semiconductor substrates.

In one embodiment, the optical property of the masking material may be a thickness, an index of refraction (or refractive index), or an extinction coefficient of the masking material or a portion of the masking material. The optical property of the masking material may be measured using a broadband radiation technique such as spectroscopic ellipsometry or spectroscopic reflectometry. The thickness of the masking material may also be measured separately using an additional optical technique, such as dual-beam spectrophotometry. Additionally, several optical properties of the masking material may be measured simultaneously. For example, a thickness of the upper, middle, and lower portions of the implanted masking material may be measured simultaneously. In addition, an index of refraction and an extinction coefficient may be measured simultaneously for the implanted masking material or a portion of the implanted masking material. Depending on the number of optical properties which are measured, several characteristics of the implanted ions may also be determined simultaneously. Characteristics of the ion implantation process may include, but are not limited to, implant dose, implant energy, and implant species. Characteristics of the implanted masking material may include, but are not limited to, concentration of the implanted ions in the masking material and the presence of implanted ions in the masking material.

In some embodiments, optical properties of masking materials formed on semiconductor substrates which have been subjected to an ion implantation process at other energy levels may also be measured. This optical property data may be analyzed and used to generate a functional relationship between an optical property of the implanted masking layer and an ion implantation processing condition such as ion implantation energy. Furthermore, the masking materials which have been implanted at various levels of an ion implantation process condition, such as implantation energy, may be analyzed to determine the characteristics of the resulting implanted masking material. For example, the implanted masking material may be analyzed using a technique such as secondary ion mass spectroscopy. In this manner, a characteristic of the resulting implanted masking material such as a concentration of ions in the implanted masking material may be determined. Therefore, a functional relationship between a characteristic of the resulting implanted masking material and the optical property which is related to the level of the ion implantation processing condition may be determined. A functional relationship may then be used to analyze subsequently formed wafers to determine a level of an ion implantation process condition or a characteristic of the resulting implanted masking material. Alternatively, mathematical or theoretical modeling may also be used to determine an implant condition or a characteristics of the implanted masking material based on the measured optical property of the implanted masking material.

In an embodiment, the measured optical property of the masking material may also be used to determine a quantity which is representative of the implantation of ions into at least a portion of a semiconductor substrate. The implantation of ions into a portion of a semiconductor substrate may be performed in subsequent ion implantation processing such as a semiconductor fabrication process. The implantation of ions into a portion of the semiconductor substrate may be performed to fabricate a feature of a semiconductor device. For example, junctions regions of a transistor may be formed by implanting dopant ions into regions of a semiconductor substrate adjacent to a gate conductor of the transistor. The measured optical property of the implanted masking material may be used to determine a characteristic of a process condition of the implantation of ions into the masking material. Process conditions of the implantation of ions into the masking material such as the implant species, implant dose, and implant energy may be substantially similar to implantation conditions that regions of the semiconductor substrate may be subjected to in subsequent processing. Therefore, the determined characteristic which is a function of the implanted masking material may be representative of the process conditions of the implantation of ions into the semiconductor substrate.

In an embodiment, the measured optical property of the implanted masking material may also be used to determine a characteristic of an implanted portion of the semiconductor substrate. The implanted portion of the semiconductor substrate may be formed during the implantation of ions into the masking material or during subsequent ion implantation processes. Characteristics of the implanted semiconductor substrate may include a depth of the implanted portion of the semiconductor substrate, a concentration of ions in the implanted portion of the semiconductor substrate, and a distribution of implanted ions as a function of the thickness of the implanted semiconductor substrate. This characteristic may also be a function of the measured optical property of the masking material. The function may describe a relationship between the optical property of the implanted masking material and the implantation of ions into the semiconductor substrate. The function may be determined experimentally by implanting a masking material and a portion of a semiconductor substrate simultaneously. The optical property of the implanted masking layer and the electrical properties of the implanted portion of the semiconductor substrate may then be measured. The electrical properties of the implanted portion of the semiconductor substrate may be related to characteristics of the implantation of ions into the semiconductor substrate such as depth of the implanted portion or distribution of the implanted ions as a function of thickness of the semiconductor substrate. A number of wafers may be processed and measured in this manner in order to generate a set of data which may be used to determine a functional relationship between an optical property of an implanted masking material and a characteristic of implanted ions in an underlying semiconductor substrate. Alternatively, the functional relationship may include a mathematical or theoretical model which describes a relationship between implantation in the masking material and implantation into the semiconductor substrate. For example, a mathematical or theoretical model may be used to determine the depth of implanted regions of a semiconductor substrate using the implant energy, the implant dose, or the depth of the implanted region of the masking material as determined by using an optical property of the implanted masking material.

In an embodiment, at least one optical property of the implanted masking material may be measured using a broadband radiation technique. Furthermore, a broadband radiation technique such as spectroscopic ellipsometry or spectroscopic reflectometry may be used to simultaneously measure several optical properties of the implanted masking material. In addition, optical properties of several portions of the implanted masking material, such as an upper, middle, and lower portion, may be measured simultaneously using a broadband radiation technique. Furthermore, optical properties of several masking material layers which may be formed on the semiconductor substrate may be measured simultaneously using spectroscopic ellipsometry or spectroscopic reflectometry. The optical properties which may be measured using a broadband radiation technique include, but are not limited to, thickness, index of refraction, and extinction coefficient. Therefore, a broadband radiation technique may be used to completely characterize the ion implanted masking material and the ion implantation process. In addition, because a broadband radiation technique may provide simultaneous measurement of several optical properties of the implanted masking material, measurements of the optical properties of the masking material using multiple devices or multiple processes may be eliminated.

Figure 9:
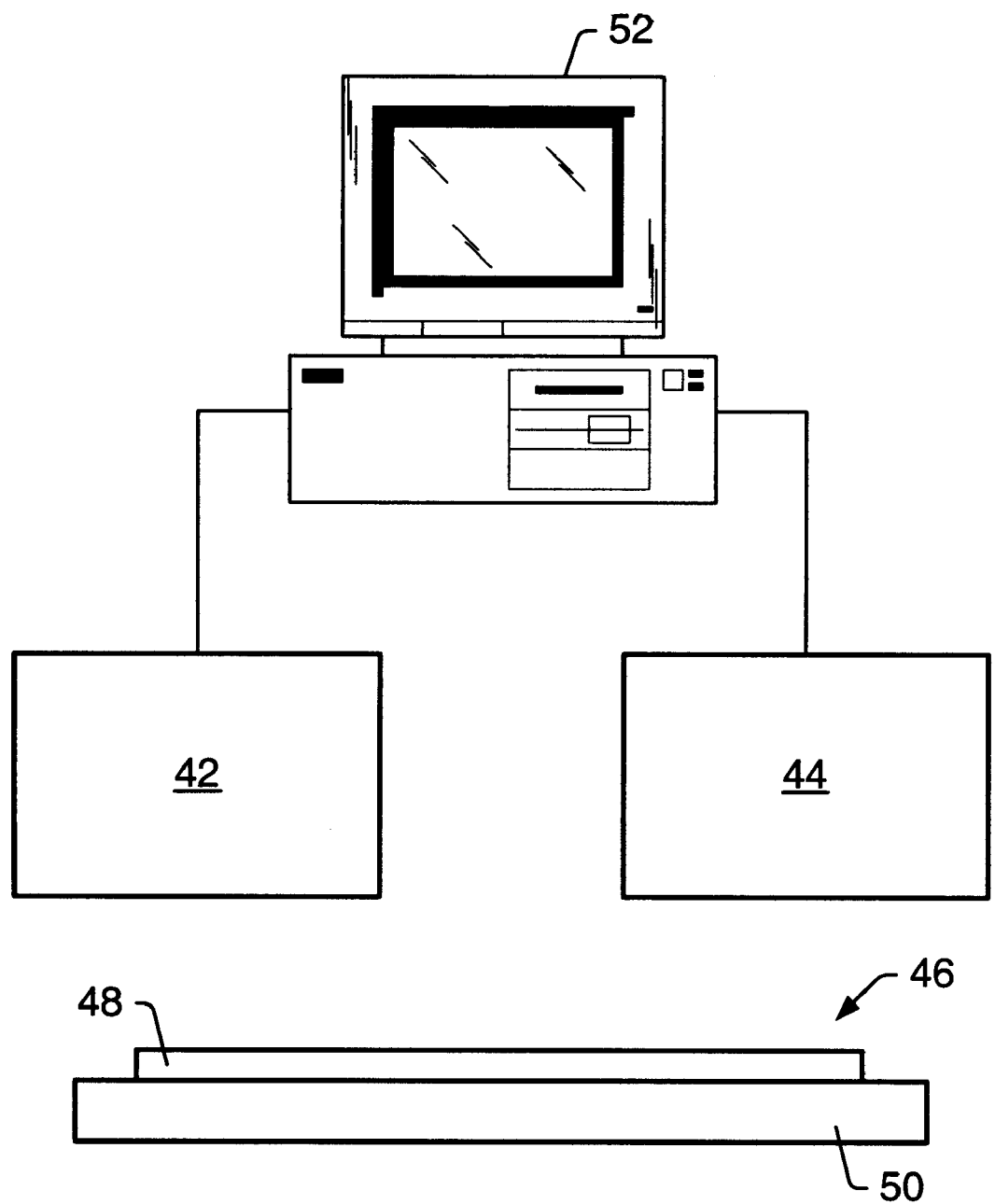
FIG. 9 depicts a schematic block diagram illustrating an embodiment of a system for inspecting a wafer.

A thickness of the implanted masking material, however, may also be measured separately from the optical property measurements. In some embodiments, for example, a system may include dual-beam device 42 and spectroscopic device 44, as shown in FIG. 9. The dual-beam device may be configured to measure a thickness of wafer 46. The wafer may include masking material 48 arranged on semiconductor substrate 50. The dual-beam device may be a dual-beam spectrophotometer which may be suitable for measuring a variety of materials having a wide range of thicknesses. The spectroscopic device may be configured to measure at least one optical property of the wafer. The spectroscopic device may be a spectroscopic ellipsometer or a spectroscopic reflectometer which may be suitable for measuring an index of refraction and an extinction coefficient of the implanted masking material across a broad spectrum of wavelengths. As such, the system may provide separate measurements of a thickness of the masking material and at least one optical property of the masking material. Furthermore, the system may also include operating system 52 which may be configured to interface with the spectroscopic device and the dual-beam device. Therefore, the operating system may also be configured to determine a characteristic of the implanted ions in the masking material as a function of the measured optical property of the masking material. The operating system may be further configured to determine a thickness of the masking material which may be a function of the measured data from the dual-beam device. One system, therefore, may be configured to perform direct measurements of the thickness of the masking material and indirect measurements of the implantation of ions into the masking material.

The term "broadband radiation" is used to indicate radiation whose frequency-amplitude spectrum includes two or more different frequency components. A broadband radiation technique may utilize a broad range of wavelengths during measurement, such as from approximately 190 nm to approximately 1700 nm. The range of wavelengths, however, may be larger or smaller depending on the tool capability. The absorption characteristics of the masking material may also determine an appropriate wavelength range. For example, a masking material may have a high absorption over a range of wavelengths and may not reflect enough light in this range of wavelengths to be detected by conventional means. The masking material, however, may also exhibit an increased sensitivity at one of more wavelengths. For example, a small change in chemical composition may cause a large change in an optical property of a masking material over a particular range of wavelengths. Therefore, the entire spectrum of wavelengths may be used to examine the masking material. The data which is used to characterize the masking material may include the entire spectrum of wavelengths or only the wavelengths at which the masking material exhibits an increased sensitivity. Depending on the technique that is being used to examine the masking material or the underlying regions of the semiconductor substrate, the data which is measured may include the polarization of the light that is reflected from the sample or the intensity of the light that is reflected from the sample.

The spectroscopic ellipsometer or reflectometer may be any device known in the art, but may preferably have a focusing mechanism such that incident light may be impinged upon only one feature of the semiconductor device. Examples of focused beam spectroscopic ellipsometry and reflectometry methods and systems are illustrated in U.S. Pat. No. 5,608,526 to Piwonka-Corle et al., U.S. Pat. NO. 5,859,424 to Norton et al., and U.S. Pat. No. 5,910,842 to Piwonka-Corle et al. and are incorporated by reference as if fully set forth herein. A feature of the semiconductor device may be, for example, a gate conductor of a transistor or a masking material over a gate conductor of a transistor. Therefore, evaluation of an ion implantation process may be performed using a reference wafer having a masking material which may be patterned in the same manner that a masking material on a product wafer may be patterned. Because the masking materials on the reference and product wafers may have similar topographies, error which may be caused by using a monitor wafer having a planar masking layer to analyze a product wafer having a non-planar patterned masking layer may also be reduced. Additionally, because ellipsometry and reflectometry are non-destructive and non-invasive testing techniques, a product wafer may also be used for evaluation of an ion implantation process. The method to evaluate an ion implantation process, therefore, may eliminate the processing steps to form reference wafers.

Spectroscopic reflectometry may include focusing a broadband radiation beam on a patterned masking material and measuring reflectance spectra, index of refraction, and, indirectly, film thicknesses. Example of spectroscopic reflectometers are illustrated in U.S. Pat. No. 4,999,014 to Gold et al., and U.S. Pat. No. 5,747,813 to Norton et al. and are incorporated by reference as if fully set forth herein. A xenon arc lamp may be used as an illumination system and may emit a light beam of visible and ultraviolet light. A sample beam may be passed through a beamsplitter mirror which may produce a continuous broadband spectrum of light. The sample beam may then be focused onto a feature of the sample wafer, and the reflected sample beam may be passed through a spectrometer. The light may be dispersed by a diffraction grating as it enters the spectrometer and the resulting first order diffraction beam of the sample beam may be collected by a linear photodiode array. The photodiode array, therefore, may measure the sample reflectance spectrum. The relative reflectance may then be obtained by dividing the sample light intensity at each wavelength by a relative reference intensity at each wavelength. A relative reflectance spectrum may then be used to determine the thickness of various films on the wafer. In addition, the reflectance at a single wavelength and the refractive index of the film may also be determined from the relative reflectance spectrum.

Spectroscopic ellipsometry may include focusing an incidence beam of polarized light on the patterned masking material and monitoring a change in polarization for the beam which is reflected from the substrate across a broad spectrum of wavelengths. Examples of spectroscopic ellipsometers are illustrated in U.S. Pat. No. 5,042,951 to Gold et al., U.S. Pat. No. 5,412,473 to Rosencwaig et al., U.S. Pat. No. 5,581,350 to Chen et al., U.S. Pat. No. 5,596,406 to Rosencwaig et al., U.S. Pat. No. 5,596,411 to Fanton et al., U.S. Pat. No. 5,771,094 to Carter et al., U.S. Pat. No. 5,798,837 to Aspnes et al., U.S. Pat. No. 5,877,859 to Aspnes et al., U.S. Pat. No. 5,889,593 to Bareket et al., U.S. Pat. No. 5,900,939 to Aspnes et al., U.S. Pat. No. 5,917,594 to Norton and U.S. Pat. No. 5,973,787 to Aspnes et al. and are incorporated by reference as if fully set forth herein. Additional examples of spectroscopic devices are illustrated in PCT Application No. WO 99/02970 to Rosencwaig et al. and is incorporated by reference as if fully set forth herein. Typically, the beam reflected from the sample may be passed through a polarizer of the spectroscopic ellipsometer. Prior to passing through the polarizer, the reflected beam may have elliptical polarization. After passing through the polarizer, the beam may be linearly polarized. The reflected light may be passed through an analyzer of the spectroscopic ellipsometer and into a dispersion element, or a spectrometer. The dispersion element may separate beam components having different wavelengths. The separated components of the beam may be detected by individual elements of a detector array. The polarizer is usually rotating such that a time varying intensity may be detected by the elements of the detector array. A processor may receive the measured data from each detector and may process the data.

An intensity of light at each detector may be converted to ellipsometric parameters $\psi$ and $\Delta$ by mathematical equations which are known in the art. The ellipsometric parameters may be typically shown as tan $\psi$ and cos $\Delta$. Tan $\psi$ is the amplitude of the complex ratio of the s and p components of the reflectivity of the sample, and $\Delta$ is the phase of the complex ratio of the s and p components of the reflectivity of the sample. The term "s component" is used to describe the component for the polarized radiation having an electrical field which is perpendicular to the plane of incidence of the reflected beam. The term "p component" is used to describe the component for the polarized radiation having an electrical field in the plane of incidence of the reflected beam. For very thin films, tan $\psi$ may be independent of thickness and $\Delta$ may be linearly proportional to the thickness.

Software capability which may be integrated into an operating system of a spectroscopic ellipsometer may be used to convert the ellipsometric parameters, ψ and Δ, to an optical property of an entire masking material, a portion of the masking material, or a multi-layer masking stack using a mathematical, or optical, model. Typically, a personal computer having a software package which is capable of rapidly performing data-fitting calculations, such as a least-squares fitting technique, may be appropriate for this use. Because ellipsometric data including ψ and Δ may be collected at small increments across a broad spectrum of wavelengths and several angles, several hundred data points may be included in the calculations. However, several software packages have been integrated into processing systems for use with spectroscopic ellipsometers that are capable of handling this large amount of data. The same processor that may be used to collected the data from the reflected light detectors may be also used to perform the iterative data-fitting calculations. Examples of such systems include operating systems of the spectroscopic ellipsometers which have been included by reference above and are typically commercially available.

There are several optical models which may be used in the analysis of the ellipsometric data. Examples, of such models include a cauchy model, a harmonic oscillator model, and a polynomial series expansion model. An appropriate model, however, may be chosen based on material characteristics, desired optical properties of the material, and the computational difficulty associated with the model. For example, the cauchy model is a relatively straightforward mathematical model to solve and to understand. The cauchy model, however, may not be valid for wavelengths at which a material exhibits absorption. Additionally, the optical properties of several masking material layers simultaneously may also be determined by using an appropriate optical model or a combination of optical models. Therefore, when using spectroscopic ellipsometry to analyze ion implanted masking layers, one optical model may be more appropriate for analysis than others.

Thickness, cauchy coefficients, indexes of refraction, and extinction coefficients for a layer, a portion of a layer, or several layers may be calculated from the ellipsometric parameters using an optical model such as the cauchy model. The cauchy coefficients may be used in a Taylor series expansion to correlate the wavelength of light that is being passed through a sample to the refractive index of the material. The cauchy coefficients remain constant over a range of wavelengths for which the material does not exhibit absorption. Therefore, the cauchy coefficients may be used to predict the refractive index of a sample over the range of wavelengths for which the material does not exhibit absorption. The index of refraction "n" is related to the speed of light as it moves through a medium and is dependent upon the wavelength of the light. The extinction coefficient "k" is also dependent upon wavelength and relates to the absorption of light. The extinction coefficient may also be used to calculate the absorption coefficient for a given wavelength. Further discussion of the ellipsometric parameters and the optical properties of materials is illustrated in U.S. Pat. No. 4,905,170 to Forouhi, et al. and is incorporated by reference as if fully set forth herein.

Optical evaluation of an ion implantation process may provide several advantages over current methods to evaluate an ion implantation process. For example, an optical method may provide non-destructive testing and may not interfere with processing of the semiconductor substrate or the performance of the fabricated semiconductor device. Furthermore, optical evaluation of the masking material may not require additional processing of the masking material or the semiconductor substrate on which the masking material is formed. Therefore, evaluation of an ion implantation process using an optical method, such as a broadband radiation technique, may be performed during the ion implantation process.

In an embodiment, a system configured to evaluate an ion implantation process may include a spectroscopic device coupled to an ion implanter. The spectroscopic device may include a spectroscopic reflectometer or a spectroscopic ellipsometer. In addition, the spectroscopic device may be coupled to the ion implanter such that the spectroscopic device may be external to the ion implanter such that delicate machinery of the spectroscopic device may be protected from harsh chemical and physical conditions within the ion implanter. Furthermore, the device may be externally coupled to the ion implanter such that the spectroscopic device does not interfere with the operation, performance, or control of the ion implantation process. The spectroscopic device, however, may be configured to focus an incident beam of broadband radiation onto the semiconductor substrate which is being implanted. The spectroscopic device may also be configured to detect and analyze a beam of broadband radiation which may be reflected and polarized from the semiconductor substrate during the implantation. For example, an ion implanter process chamber may be retrofitted such that small sections of a substantially optically transparent material may be disposed within walls of the process chamber. The small sections of transparent material may enable the incident and reflected beams of broadband radiation to travel from an illumination system outside the process chamber to a semiconductor substrate within the process chamber and from the semiconductor substrate to a detection system outside the process chamber. The optically transparent material may have additional optical or material properties such that a broadband radiation beam may be passed through the transparent sections of the process chamber without undesirably altering the optical properties of the incident and reflected beam. The configuration of an ion implanter, however, may determine an appropriate method to couple the spectroscopic device to the ion implanter. For example, the placement and dimensions of the transparent material sections disposed within the walls of the process chamber may be depend on the configuration of the components within the process chamber. Therefore, a spectroscopic device coupled to an ion implanter may be configured to measure optical properties of the masking material, optical properties of a portion of the masking material, optical properties of a multi-layer masking stack, or optical properties of the semiconductor substrate during the implantation process.

In an additional embodiment, the system may also include an operating system which may be coupled to the spectroscopic device and the ion implanter. The operating system may be configured to interface with the spectroscopic device and the ion implanter. The operating system may receive data from the ion implanter which may be representative of the operating parameters of an ion implantation instrument used to implant ions into a masking material or a semiconductor substrate. The operating system may also be configured to receive data from the spectroscopic device which may be representative of at least one optical property. Additionally, the operating system may be further configured to control the spectroscopic device and the ion implanter. For example, the operating system may alter a characteristic of the implanted ions by altering a parameter of an instrument coupled to the ion implanter. Therefore, the system may monitor and control the implantation of ions during a process.

In an additional embodiment, the system may be configured to monitor or measure variations in at least one optical property of the implanted masking material. The spectroscopic device may be configured to measure the optical property of the implanted masking material substantially continuously or at predetermined time intervals. The operating system may, therefore, receive the optical property data from the spectroscopic device and monitor variations in the optical property over the duration of the ion implantation process. By analyzing the variations in the optical properties of the masking material during implantation, the operating system may also generate a signature which may be representative of the implantation of the ions into the masking material. The signature may include at least one singularity which may be characteristic of an endpoint of the ion implantation process. An appropriate endpoint for an ion implantation process may be a predetermined concentration of ions in the masking material or in the semiconductor substrate. In addition, the predetermined concentration of ions may be larger or smaller depending upon the semiconductor device feature which is being fabricated by the ion implantation process. After the operating system has detected the singularity of the signature, the operating system may stop the implantation of ions by altering a level of a parameter of an instrument coupled to the ion implanter.

In an embodiment, a method for fabricating a semiconductor device may include implanting ions into a masking material and a semiconductor device. The masking material may be arranged on the semiconductor device such that predetermined regions of the semiconductor device may be implanted with ions. For example, portions of the masking material may be removed using a lithographic process which may expose regions of the semiconductor substrate to the implantation process. The predetermined regions may be regions of the semiconductor substrate in which features of a semiconductor device are to be formed. Fabricating a semiconductor device may also include monitoring the implantation of ions into the semiconductor substrate by measuring at least one optical property of the masking material during the ion implantation process. The optical property of the masking material may be altered by the implantation of ions into the masking material. As such, the method for fabricating a semiconductor device may also include determining at least one characteristic of the implanted ions in the semiconductor substrate. The characteristic may be determined using a function which describes the relationship between the optical property of the implanted masking material and the implantation of ions into the semiconductor substrate.

A system as described in an above embodiment may be used to measure the optical property of the masking material and to measure variations in the optical property of the masking material. The system may also be used, therefore, to control the ion implantation process in response to the optical property of the masking material by altering a parameter of an instrument which is coupled to the ion implanter. Variations in the optical property may also be monitored by the system during the ion implantation process and may be used to generate a signature of the ion implantation process. An endpoint may be determined by a singularity which may be observed in the signature of the process. In an embodiment, therefore, the semiconductor fabrication process may also include controlling the ion implantation process in response to the measured optical property of the masking material and detecting an endpoint of the ion implantation process.

In an embodiment, any material that is substantially transparent to at least a portion of the light produced by an optical inspection device may be used as a masking material for evaluation of an ion implantation process involving measurement of optical properties of a masking material. During an ion implantation process, typically, the entire wafer may be scanned with a beam of dopant ions. Prior to the ion implantation process, therefore, portions of the masking material may be removed in a predetermined pattern using a lithographic or etch process to selectively expose regions of the semiconductor substrate. The remaining portions of masking material may inhibit the passage of dopant ions into underlying regions of the semiconductor substrate during an ion implantation process. For example, a dielectric material overlying a gate conductor during an ion implantation process may prevent implantation of ions into the gate conductor or the channel region beneath the gate conductor. As such, patterning the masking material may provide selective implantation of ions into exposed regions of the semiconductor substrate. The exposed regions of the semiconductor substrate may, therefore, correspond to a particular feature of the semiconductor device which is being fabricated such as a junction region. Alternatively, ions may be implanted through a masking material and into underlying regions of the semiconductor substrate. In this manner, the masking material may include a thin gate dielectric material arranged over junction regions of a transistor. Implantation of ions through a masking material may enhance the electrical properties of the implanted region of the semiconductor substrate, for example, by randomizing the directional paths of the ions which are being driven into the semiconductor substrate. The masking material may also be formed over a substantially planar semiconductor substrate or over a non-planar semiconductor topography.

In one embodiment, the masking material may be a resist material. Resist materials may typically be deposited on a semiconductor substrate by spin coating and may typically be patterned by a lithography technique. Resist materials may include photoresist materials which may be patterned by an optical lithography technique. Other resist materials, however, may also be used such as e-beam resists or X-ray resists which may be patterned by an e-beam or an X-ray lithography technique, respectively. In another embodiment, the masking material may be composed of an inorganic material. Inorganic masking materials that may be used to inhibit ion implantation include, but are not limited to silicon dioxide, silicon nitride, titanium nitride, polycrystalline silicon, cobalt silicide or titanium silicide. The inorganic masking material may be formed by deposition techniques, such as chemical vapor deposition, or thermal growth techniques. The inorganic masking materials may be patterned using an etch technique.

In another embodiment, the masking material may include two or more layers of different masking materials arranged in a stack. In one embodiment, the masking stack may include a resist layer formed upon an inorganic masking material layer. The inorganic masking layer may be formed from any material that aids in inhibiting the implantation of ions through the masking stack. When used as part of a masking stack, the inorganic material need not be transparent or exhibit any changes in optical properties when exposed to ions. The subsequent optical analysis may be done on the overlying resist material, rather than on the underlying inorganic masking material. The inorganic masking layer may be formed on the semiconductor substrate prior to coating the semiconductor substrate with a resist material. This additional inorganic layer, in combination with an overlying resist layer, may serve as the masking stack. Different masking layers may be more appropriate in some embodiments depending on the particular processing or device configuration. The selection of the masking material is typically driven by the type ion implantation process being used.

During ion implantation processes, and especially in processes using high dosage levels, the semiconductor substrate may also experience significant damage due to the implantation of dopant ions into regions of the semiconductor substrate. After processing, the implanted portion of the semiconductor substrate may typically be composed of an upper crystalline damaged layer and an intermediate layer of amorphous silicon. The damage in the upper crystalline layer may be caused, for example, by electronic collisions between atoms of the silicon layer and the implanted ions. Displacement damage, however, may not be produced if the ions entering the silicon layer do not have enough energy per nuclear collision to displace silicon atoms from their lattice sites. Damage to the silicon by the implanted ions may produce an amorphous layer below the upper crystalline damaged layer. Increasing the dose of ions, and in particular heavy ions, may produce an amorphous region in which the displaced atoms per unit volume approach the atomic density of the semiconductor. As the implant dose of the ion implantation process increases, the thickness of the amorphous layer may also increase. The presence of an amorphous layer of silicon may act as a boundary which may reflect optical radiation. The reflection of light by the amorphous layer may also effect the reflectance and ellipsometric measurements. Therefore, measurement of an optical property of the amorphous silicon layer may also be used to monitor the processing conditions of an ion implantation process.

In an embodiment, an optical property of an implanted portion of a semiconductor substrate may be measured. The optical property may be a thickness, an index of refraction, or an extinction coefficient of the implanted portion. In addition, several optical properties of the implanted portion of the semiconductor substrate may be measured substantially simultaneously. The optical property of the implanted portion of the semiconductor substrate and the optical property of the implanted masking material may also be measured substantially simultaneously. A characteristic of the implanted ions in the semiconductor substrate may be determined as a function of the measured optical property of the implanted portion of the semiconductor substrate. This characteristic may, therefore, be directly related to the implantation of ions into a portion of the semiconductor substrate or a characteristic of the resulting implanted semiconductor substrate. For example, the characteristic may be an implant energy, an implant dose, or an implant species which may be involved in the ion implantation process. In addition, the characteristic may be a concentration of ions, a depth, a distribution of the implanted ions as a function of thickness, or a presence of the implanted ions in the implanted portion of the semiconductor substrate. In addition, optical properties of the implanted portion of the semiconductor substrate may be used to determine several characteristics substantially simultaneously which may include, but are not limited to, characteristics of the implantation of ions or characteristics of the implanted semiconductor substrate described above. The characteristics of the semiconductor substrate may also be determined at substantially the same time that the characteristic of the implanted ions in the masking material is determined.

In an additional embodiment, optical properties of the implanted portion of the semiconductor substrate may be measured using a broadband wavelength technique as described in the measurement of the optical properties of the implanted masking material. For example, a broadband wavelength technique may be used which may involve using a spectroscopic device such as a spectroscopic ellipsometer or a spectroscopic reflectometer to measure the optical properties of the implanted portion of the semiconductor substrate. Additionally, the spectroscopic device may be coupled to an ion implanter such that measuring the optical properties of the implanted portion of the semiconductor substrate may be performed during an ion implantation process. Therefore, variations in the optical property of the implanted portion of the semiconductor substrate may also be measured during the an ion implantation process. In this manner, a signature characterizing the implantation of ions into the semiconductor substrate may be obtained. This signature may also include a singularity which is characteristic of an end of the implantation process. As described above, therefore, an appropriate endpoint may be, for example, a predetermined concentration of ions in the semiconductor substrate. In addition, the predetermined concentration of ions may be larger or smaller depending upon the feature of a semiconductor device which is to be fabricated. An appropriate operating system, as described in an above embodiment, may then stop processing of the semiconductor substrate by controlling the operation of the ion implanter.

In an embodiment, the measured optical properties of the implanted masking material may then be used to determine appropriate processing conditions for subsequent ion implantation processes of additional semiconductor substrates or product wafers. For example, the implant energy of the implantation of ions into the masking material may be determined using the measured optical property of the implanted masking material. The determined implant energy may then be used to determine the depth that ions may be implanted into a semiconductor substrate during an ion implantation process. The depth of the implanted portion of the semiconductor substrate may also be determined directly from the measured optical properties of the implanted portion of the semiconductor substrate. The determined depth of the implanted portion of the semiconductor substrate may be less than a predetermined depth in a semiconductor substrate. The predetermined depth may be dependent on the feature which may be fabricated during the ion implantation process. Therefore, before processing additional semiconductor substrates, or product wafers, the implant energy or another process condition of the ion implantation process may be altered to achieve the predetermined depth of the implanted region of the semiconductor substrate. In this example, the implant energy of the ion implant process may be increased to drive the ions deeper into the semiconductor substrate. In this manner, a feedback process control method may be provided which may include using the measured optical properties of a masking material to determine the process conditions of an ion implantation process to fabricate semiconductor devices. In an additional embodiment, a feedback process control method may include using the measured optical properties of an implanted portion of a semiconductor substrate to determine process conditions of an ion implantation process to fabricate semiconductor devices.

In an additional embodiment, the measured optical properties of the implanted masking material may be used to determine process conditions of additional semiconductor fabrication processes which may be performed subsequent to the ion implantation process. The additional semiconductor fabrication processes may include a process to anneal the implanted regions of the semiconductor device or a process to remove the masking material. For example, the implant energy of the implantation of ions into the masking material may be determined using the measured optical property of the implanted masking material. The determined implant energy may be used to determine the depth that ions may be implanted into a semiconductor substrate using the current process conditions of the ion implantation process to fabricate product wafers. Alternatively, the depth of the implanted portion of a semiconductor substrate may also be determined directly using a measured optical property of the implanted semiconductor substrate. The determined depth of the implanted portion of the semiconductor substrate may be greater than a predetermined depth in a semiconductor substrate. The current process conditions of the subsequent annealing process may be optimized for the predetermined depth of the implanted region in the semiconductor substrate. Therefore, before annealing the implanted semiconductor substrates, or product wafers, a process condition of the annealing process such as anneal time or anneal temperature may be altered such that recrystallization of the entire amorphous silicon layer may be performed. In this example, the anneal time may be increased to ensure complete recrystallization of the amorphous layer which may be formed in the semiconductor substrate. In this manner, a feedforward process control method may be provided which may include using the measured optical properties of a masking material to determine the process conditions of a semiconductor fabrication process which may be performed subsequent to an ion implantation process. The feedforward process control method may also include using the measured optical properties of an implanted portion of the semiconductor substrate to determine the process conditions of a semiconductor fabrication process which may be performed subsequent to an ion implantation process.

A set of data may be collected and analyzed that may predict the processing conditions, or a change in processing conditions, based on an optical property of the masking material. Process control methods described herein may also be used to further optimize the process by using optical testing in conjunction with electrical testing to analyze the device performance. The combination of optical and electrical analysis may provide a larger amount of characterization data for an ion implantation process. The characterization data may be used to understand the mechanisms of ion implantation, to pin-point the cause of defects, and to make accurate adjustments to the processing conditions. In addition, this process control strategy may be used to qualify, or characterize the performance of, a new ion implant tool. The process control method may also be used to compare the performance of several similar tools. This may be particularly important in a manufacturing environment in which several tools may be used in parallel to manufacture one device or product. Furthermore, this process control strategy may be used to determine an appropriate masking layer material and thickness in the development stage for an ion implantation process.

Turning now to the drawings, FIG. 1 illustrates an embodiment of a method to evaluate an ion implantation process. As shown in step 10, a first semiconductor substrate having a first masking layer arranged over at least a portion of the first semiconductor substrate may be subjected to an ion implantation process using first ion implantation processing conditions to form a reference wafer. The semiconductor substrate may typically be monocrystalline silicon but may also be any substrate that has a substantially reflective surface. In an ion implantation process, processing conditions may include implant species, implant dose, implant energy, angle of implantation, and temperature of the implantation process. The implantation process conditions may be chosen to create an implanted region in the semiconductor substrate having a predetermined ion concentration. The factors for generating a predetermined ion concentration may be related to the processing conditions as well as the material the implants are being formed within. The first ion implantation processing conditions may be characterized and verified for the production of a known ion implant concentration. The verification of the first processing conditions may be performed by a post-process characterization of the semiconductor substrate or topography. Post process characterization may include any metrology technique, such as electrical testing or secondary ion mass spectroscopy.

A second semiconductor substrate having a second masking material arranged over at least a portion of the second semiconductor substrate may be processed using a second set of ion implantation processing conditions to form a product wafer as shown in step 14. In one embodiment, the operating parameters of an ion implantation instrument used to produce product wafers may be set to the same operating parameters of an ion implantation instrument used to produce the reference wafer. Theoretically, the product wafer should have the same ion implantation concentration as the reference wafer. Although the same process parameters may be used for the production of the product and reference wafers, over time the produced process conditions may begin to drift outside of a design tolerance for the ion implantation process. This drift may occur despite using the same operating parameters for the ion implantation instrument. For an ion implantation process, this drift may be due to contamination, beam neutralization, secondary-electron emission, or scan lock-up.

Frequent monitoring of manufacturing processes may be implemented to ensure that a tool is operating to produce wafers that meet the design tolerances. The design tolerance of a process or device is related to the acceptable amount of error allowed for the process or device. For ion implantation processes, the design tolerance may be related to the concentration of ions implanted into the substrate. In this case, the design tolerance may be predefined by a range of acceptable concentrations for the implanted ions. Any concentration of ions that falls outside of this predefined range will be considered to be outside the design tolerance of the ion implantation process. As the feature sizes of semiconductor devices shrink, the design tolerances of semiconductor fabrication processes must also be reduced to ensure that substantially defect-free and working semiconductor devices are fabricated. Therefore, drift in the performance of a tool alone may be large enough to cause an ion implantation process or device to be outside of the design tolerance and may significantly reduce the yield of working semiconductor devices. Monitoring the drift of tool performance and altering the process conditions of semiconductor fabrication process is, therefore, becoming increasingly important to successful fabrication of semiconductor devices.

At least one optical property of the first and second masking materials formed on the first and second semiconductor substrates respectively may be measured using a broadband radiation technique, such as spectroscopic ellipsometry or spectroscopic reflectometry, as shown in steps 12 and 14 respectively. In addition, if the processing conditions are set to implant dopant ions into regions of the semiconductor substrate underlying the masking material, the optical properties of the masking material and the semiconductor substrate may be measured in steps 12 and 14. The optical property of the second masking material on the first product wafer may be compared to the optical property of the first masking material on the reference wafer. The optical properties of the first and second semiconductor substrates may also be compared.

As shown in steps 20 and 22, respectively, if the optical properties of the masking materials of the reference and the product wafer are substantially the same, or if the optical properties of the masking material and the underlying semiconductor substrate of the reference wafer and the product wafer are substantially the same, then manufacturing may proceed using the standard processing conditions. Alternatively, as shown in steps 24 and 26, if the optical properties of the masking materials of the reference and the product wafer are substantially different or if the optical properties of the masking material and the underlying semiconductor substrate of the reference wafer and the product wafer are substantially different, one or more of the processing conditions my be altered before additional product wafers are processed. After altering the processing conditions, but prior to proceeding with manufacturing, the process control procedure may be repeated by processing a second product wafer using the altered processing conditions. Steps 14 through 18 of the process control method may be repeated for the second product wafer. In this manner, an iterative strategy may be used to control the drift of the performance of an ion implantation process. The extent of the variation in an optical property of a masking layer, however, may also be small enough that the process may be determined to be within a design tolerance of the process. Periodic evaluation, such as for each lot of product wafers, may be performed in order to monitor any additional changes in the performance of the ion implantation process. In this manner, the process control method may also be used to monitor manufacturing processes for operator or random error.

Figure 2:
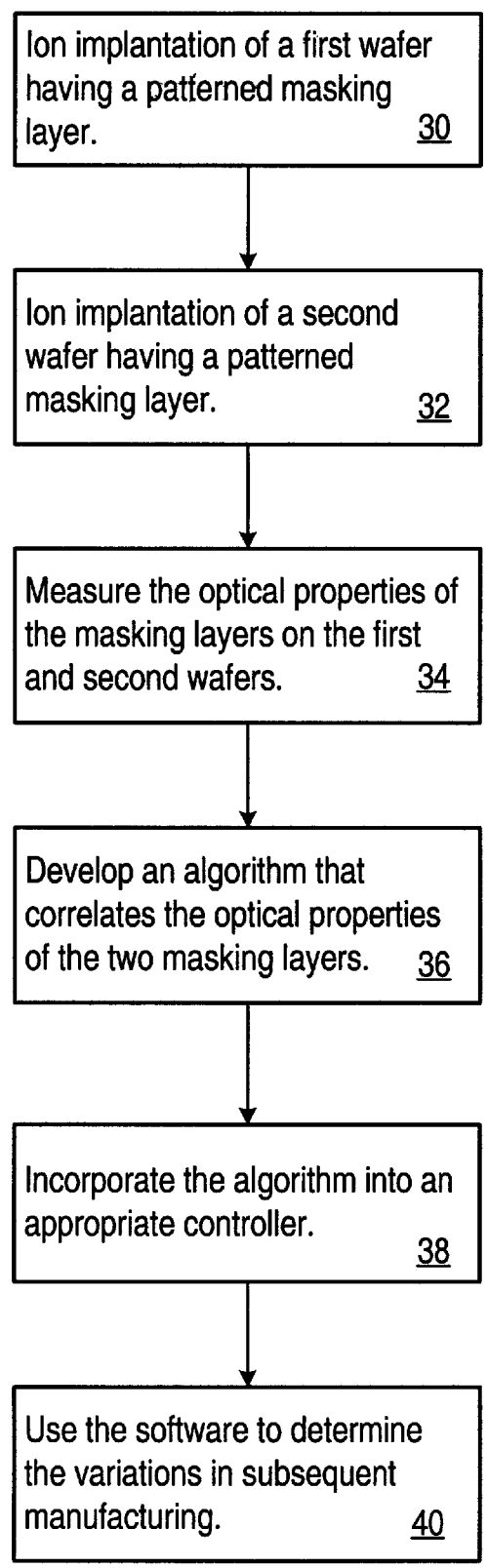
FIG. 2 depicts a flow chart illustrating a process control method to develop an algorithm that describes a quantitative relationship between ion implantation processing conditions and an optical property of a masking material which may be measured by spectroscopic ellipsometry or reflectometry.

FIG. 2 illustrates another embodiment of a method to evaluate an ion implantation process. In step 30, a reference wafer may be produced from a first semiconductor substrate having a patterned masking material that undergoes an ion implantation process. First ion implantation processing conditions may be used to process the first semiconductor substrate. As shown in step 32, a product wafer may be produced from a second semiconductor substrate having substantially the same patterned masking material. The product wafer may be formed as described above. Second ion implantation processing conditions, however, may be used to process the second semiconductor substrate. The second ion implantation processing conditions, may be the same as the first processing conditions except for a variation in at least one parameter of an ion implantation instrument. For example, the implant dose that is used to process the second semiconductor substrate may be lower than the implant dose that is used to process the first semiconductor substrate. By varying one of the ion implantation processing conditions, the masking material and the semiconductor substrate of the reference and product wafers may undergo different chemical changes. The optical properties of the patterned masking material on the reference wafer and the product wafer may then be measured. In one embodiment, an optical property of the masking material may be measured using a broadband radiation technique such as spectroscopic ellipsometry or spectroscopic reflectometry as shown in step 34. The optical properties of both masking materials may be measured as described in the above embodiment. Alternatively, the optical properties of the masking material and the underlying silicon substrate may also be measured. The optical properties included in the analysis may be any of the properties previously described.

As shown in step 36, a quantitative relationship may be developed between the processing condition that was varied and the measured variations in an optical property of the masking material or in the optical properties of the masking material and the underlying semiconductor substrate. Additional substrates may be also be processed using additional variations of the same processing parameter. For example, a third semiconductor substrate may be processed using an implant dose that is lower than the implant dose that was used to process the second semiconductor substrate. All other processing conditions may remain constant, and a correlation between the implant dose and an optical property of the masking material or optical properties of the masking material and the underlying semiconductor substrate may be developed. In this manner, an algorithm that describes the quantitative relationship between each of the process parameters for a given process and the measured optical property of the masking layer may be determined. The developed algorithms may be used during processing of product wafers to determine if the process is operating within design tolerance for that process and tool. Additionally, algorithms may be developed and used to further optimize a current process, to characterize a new tool, or to develop processes to fabricate next generation devices.

Furthermore, as shown in step 38, this algorithm may then be integrated into a controller for an optical inspection device (e.g., a spectroscopic ellipsometer or a spectroscopic reflectometer) or an ion implantation device that includes an optical inspection device. The controller may by a computer system configured to operate software to control the operation of an optical inspection device such as a spectroscopic ellipsometer or a spectroscopic reflectometer. The computer system may include a memory medium on which computer programs for operating the device and performing calculations related to the data collected. The term "memory medium" is intended to include an installation medium, e.g., a CD-ROM, or floppy disks, a computer system memory such as DRAM, SRAM, EDO RAM, Rambus RAM, etc., or a non-volatile memory such as a magnetic media, e.g., a hard drive, or optical storage. The memory medium may comprise other types of memory as well, or combinations thereof. In addition, the memory medium may be located in a first computer in which the programs are executed, or may be located in a second different computer that connects to the first computer over a network. In the latter instance, the second computer provides the program instructions to the first computer for execution. Also, the computer system may take various forms, including a personal computer system, mainframe computer system, workstation, network appliance, Internet appliance, personal digital assistant (PDA), television system or other device. In general, the term "computer system" may be broadly defined to encompass any device having a processor which executes instructions from a memory medium.

The memory medium preferably stores a software program for the operation of the optical inspection device. The software program may be implemented in any of various ways, including procedure-based techniques, component-based techniques, and/or object-oriented techniques, among others. For example, the software program may be implemented using ActiveX controls, C++ objects, JavaBeans, Microsoft Foundation Classes (MFC), or other technologies or methodologies, as desired. A CPU, such as the host CPU, executing code and data from the memory medium comprises a means for creating and executing the software program according to the methods described above.

Various embodiments further include receiving or storing instructions and/or data implemented in accordance with the foregoing description upon a carrier medium. Suitable carrier media include memory media or storage media such as magnetic or optical media, e.g., disk or CD-ROM, as well as signals such as electrical, electromagnetic, or digital signals, conveyed via a communication medium such as networks and/or a wireless link.

The software for the optical inspection device may then be used to monitor and predict the processing conditions of subsequent ion implantation process as shown in step 40. Preferably, the predefined algorithm for an ion implantation process may be incorporated into the software package which interfaces with the spectroscopic ellipsometer or reflectometer system. In this manner, the software may be configured to receive the reflectance data or ellipsometric data which may be measured by the spectroscopic ellipsometer or reflectometer. The software may also be configured to perform appropriate calculations to convert the reflectance or ellipsometric data into optical properties of the masking material or the masking material and the underlying semiconductor substrate. The software may be further configured to select and use an appropriate optical model to convert the reflectance or ellipsometric data into an optical property. Additionally, the software may also be configured to compare an optical property of a product wafer to an optical property of a reference wafer for an ion implantation process. In this manner, the software may be configured to convert variations in the optical properties to variations that may occur in the process conditions. Furthermore, by incorporation of the appropriate algorithm, the software may also be configured to convert the optical properties of a masking material into meaningful data about the process conditions of the ion implant process including characteristic of implanted ions in the masking material or the semiconductor substrate, such as implant dose or implant energy.

Evaluating a semiconductor manufacturing process by spectroscopic reflectometry or spectroscopic ellipsometry may provide several advantages over typical evaluation testing methods. These testing methods are non-invasive and non-destructive, therefore, a product wafer may be used for testing without destroying the wafer. Non-destructive testing of product wafers may be advantageous for several reasons. A test procedure using a product wafer may provide more accurate information about the performance of a tool and a process than a testing procedure that is performed on a monitor wafer. Additionally, by reducing the number of product wafers that are destroyed in evaluation testing, the overall cost of manufacturing may be reduced. Similarly, fabricating monitor wafers requires time and money resources that may be saved if evaluation of semiconductor manufacturing processes may be done using non-sacrificial product wafers.

Another advantage of using spectroscopic reflectometry or spectroscopic ellipsometry to evaluate a semiconductor manufacturing process may include rapid testing times compared to typical process control testing methods. Evaluation of a masking material using spectroscopic ellipsometry or reflectometry, across even a very broad range of wavelengths, may typically be a relatively rapid procedure. Therefore, a process may be quickly evaluated, and adjusted if necessary, before additional product wafers are processed incorrectly. In addition, quick evaluation of a process may also enable subsequent processes to be altered in response to the results of the evaluation of the masking material. In this manner, both feedback and feedforward process control may be enabled by using this method to evaluate a semiconductor fabrication process. Furthermore, using this method to evaluate a semiconductor fabrication process may also enable more frequent testing of product wafer lots, such that tighter process control may be maintained. The capability to maintain a process within a tighter tolerance may also improve yield and drive manufacturing costs down.

Additionally, spectroscopic reflectometry and spectroscopic ellipsometry may not require electrical testing of the impurity regions. Therefore, the processing steps to electrically activate these regions may be substantially eliminated. For example, electrically activating these regions may involve stripping the masking material and subjecting the semiconductor substrate to a rapid thermal process or annealing process. Therefore, conventional testing may be replaced with a method to evaluate a semiconductor manufacturing process which may eliminate several processing steps and the costs associated with performing these processing steps. Furthermore, because the testing may be done prior to electrical activation, a product wafer may be reprocessed if the process is determined to be outside of the design tolerances. In this manner, the number of incorrectly processed product wafers may also be reduced which may result, in turn, in a higher manufacturing yield and lower manufacturing costs.

Using spectroscopic reflectometry or spectroscopic ellipsometry to evaluate a semiconductor may also provide more information about the masking material compared to typical process control testing methods. A thin film measurement system using these optical techniques may provide, for example, simultaneous measurement of a thickness of a single or multiple layer stack, an index of refraction, an extinction coefficient or any other parameter of the optical models for the ion implanted masking material. Any of these material characteristics may be correlated to the implantation dose, implantation energy or other process conditions. Furthermore, because a large quantity of information about masking materials which may be involved in a semiconductor process may be provided by these techniques, this information may be used to further optimize the process, to characterize a new tool, or to develop processes to fabricate next generation devices.

Spectroscopic reflectance and ellipsometry test methods may also provide increased sensitivity due to the broadband wavelength radiation source that these methods employ. For example, a material may exhibit an optimum sensitivity at a particular wavelength or radiation regime, and different materials may be more sensitive at distinctly different wavelengths or radiation regimes. Therefore, a single layer or a multiple stack layer may be analyzed across a spectrum of wavelengths, and the optimum wavelength for characterization may be determined at which the masking material exhibits the greatest sensitivity. Additionally, the same testing procedure may be used to analyze different materials while still capturing data at the best wavelength for each material. Similarly, when analyzing a multiple stack layer using a broadband radiation source, each individual layer may be analyzed at its optimum wavelength in a single test. Accordingly, spectroscopic testing methods may provide a testing method with greater sensitivity than test methods involving single wavelength radiation sources.

EXAMPLE

Effect of Ion Implantation on the Optical Properties of a Resist

Two wafers were spin coated with a resist material having a thickness of 2.3 microns. The resist on both wafers was patterned using a lithographic technique. The wafers were subjected to two different ion implantation processes. A first ion implantation was performed on one of the two wafers using an arsenic ion implantation process having an implant energy of 300 KeV. A second ion implantation was performed on the second of the two wafers using an arsenic ion implantation process having an implant energy of 700 KeV. All other ion implantation processing parameters were the same for the processing of both wafers. For example, in both processes the implant dose was $5 \times 10^{13}$ atoms/cm$^3$.

Figure 3:
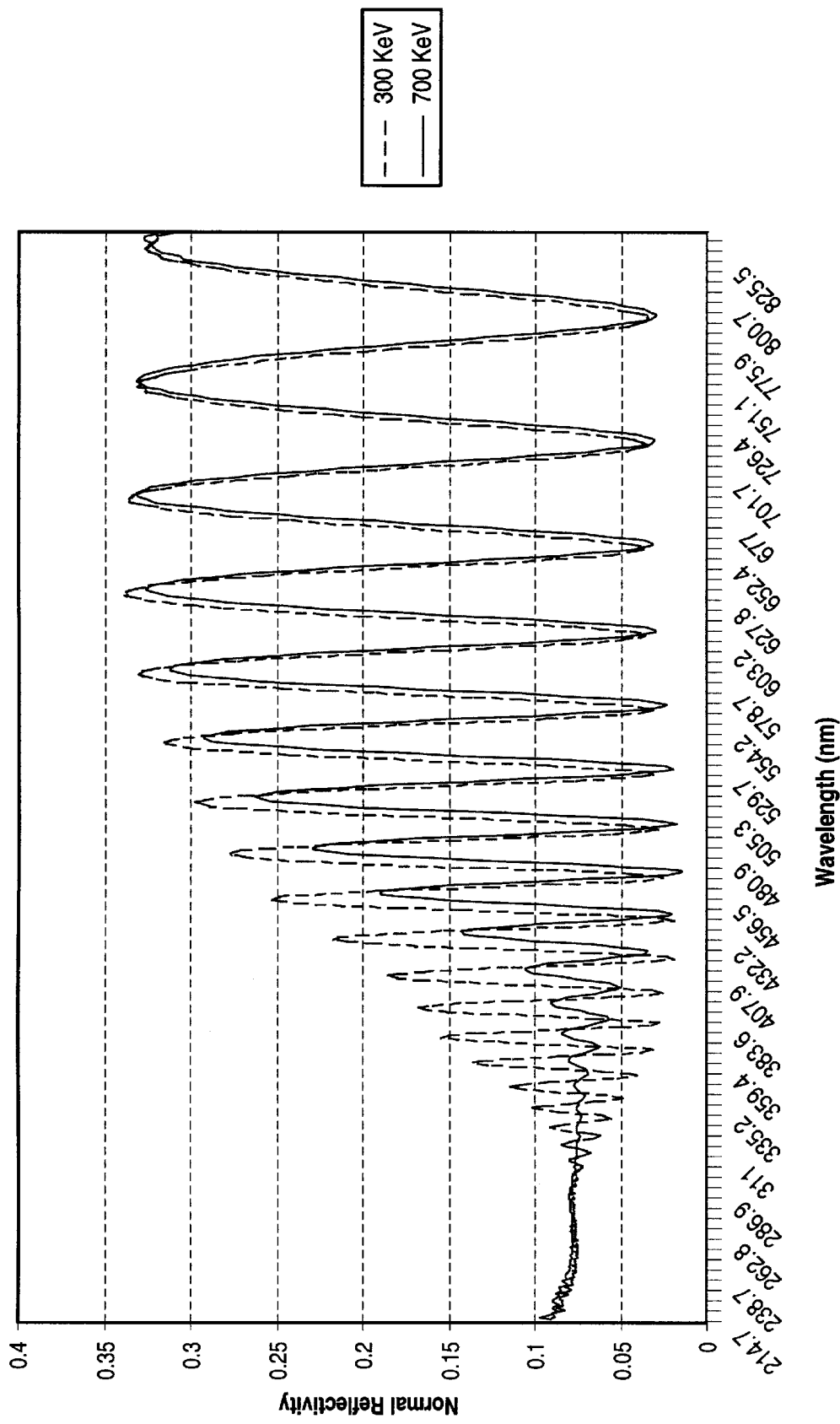
FIG. 3 depicts a plot of reflectance data versus wavelength at various implant energies for an arsenic implantation process.

The two wafers were then examined using a spectroscopic reflectometer which is integrated in a system which is commercially available from KLA-Tencor, Corporation, San Jose, Calif. (Model No. UV1280). The incident beam was focused on the patterned resist and the normal reflectivity was measured as a function of wavelength. A plot of this data is shown in FIG. 3. Larger variations in the frequency and amplitude of the normal reflectance data for the two wafers are observed in a wavelength range of approximately 300 nm to approximately 600 nm. The optical properties of the masking material, therefore, exhibit an increased sensitivity to this range of wavelengths.

In a second experiment, the effect of dopant energy on the optical properties was examined using a different dopant ion. For example, two additional wafers were patterned with a resist material as described above. The wafers were then subjected to two different ion implantation processes involving the implantation of boron instead of arsenic. A first ion implantation process was performed on one of the two wafers involving boron implantation using an energy of 300 KeV. A second ion implantation involving boron implantation was performed on the second of the two wafers using an energy of 700 KeV. All other ion implantation processing parameters were the same for the processing of both wafers including, for example, an implant dose of $5 \times 10$ atoms/cm$^3$.

Figure 4:
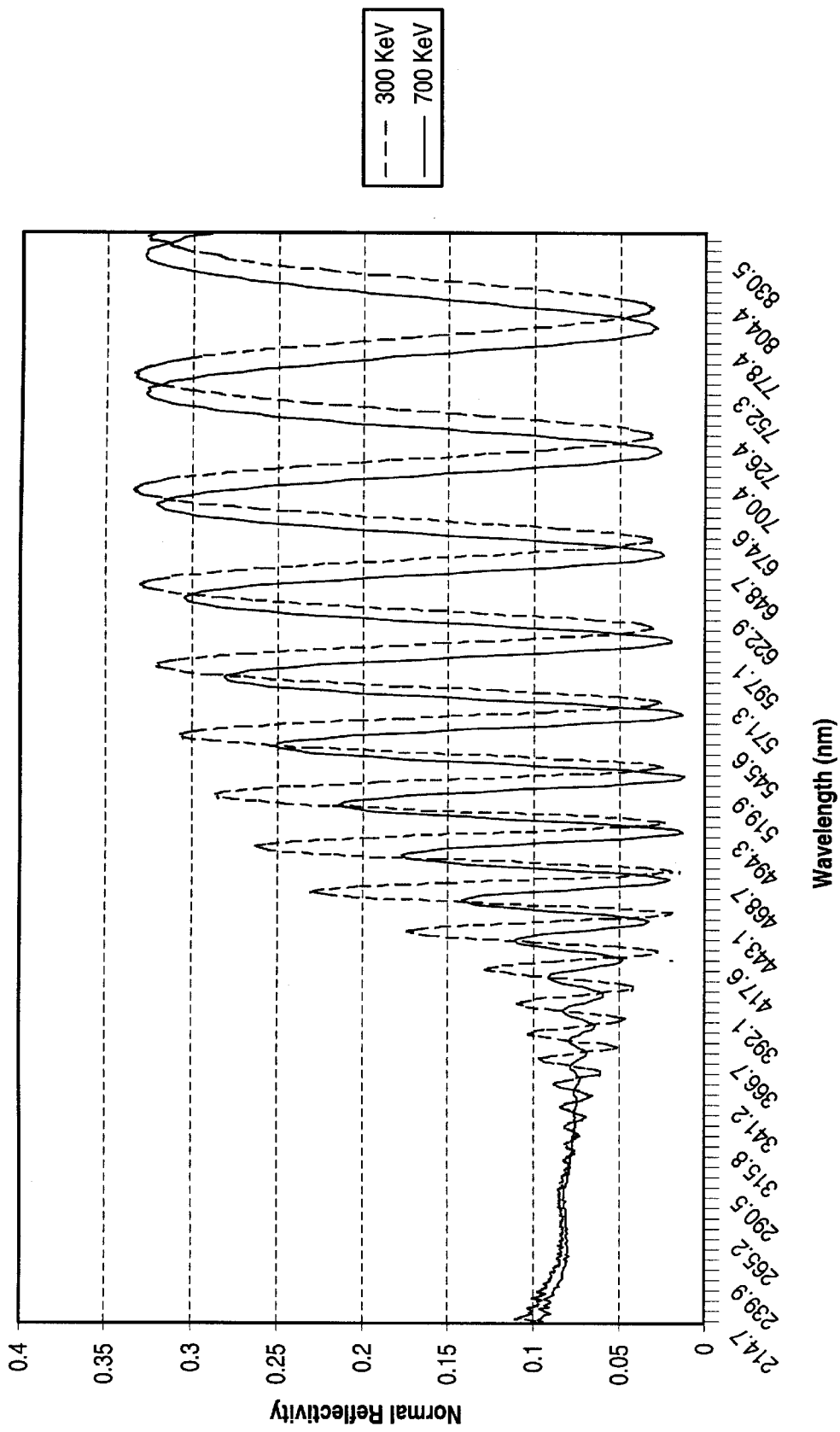
FIG. 4 depicts a plot of reflectance data versus wavelength at various implant energies for a boron implantation process.

The two wafers were analyzed using spectroscopic reflectometry using the UV1280 tool. The spot size of the incident beam was focused on the patterned resist and the normal reflectivity was measured as a function of wavelength. As shown in FIG. 4, the reflectance data for the resist was measured across a broad wavelength spectrum. The plot of this data shows that larger variations in the frequency and amplitude of the reflectance data are present at a smaller wavelength range. In this experiment, the resist shows an increased sensitivity to the wavelength range from approximately 350 nm to approximately 600 nm. Therefore, the reflectance data across the entire spectrum of wavelengths may be included in the optical modeling, or only the reflectance data across the spectrum of increased sensitivity may be included in the optical modeling. The modeling may also be performed as described in the above experiment.

Figure 5:
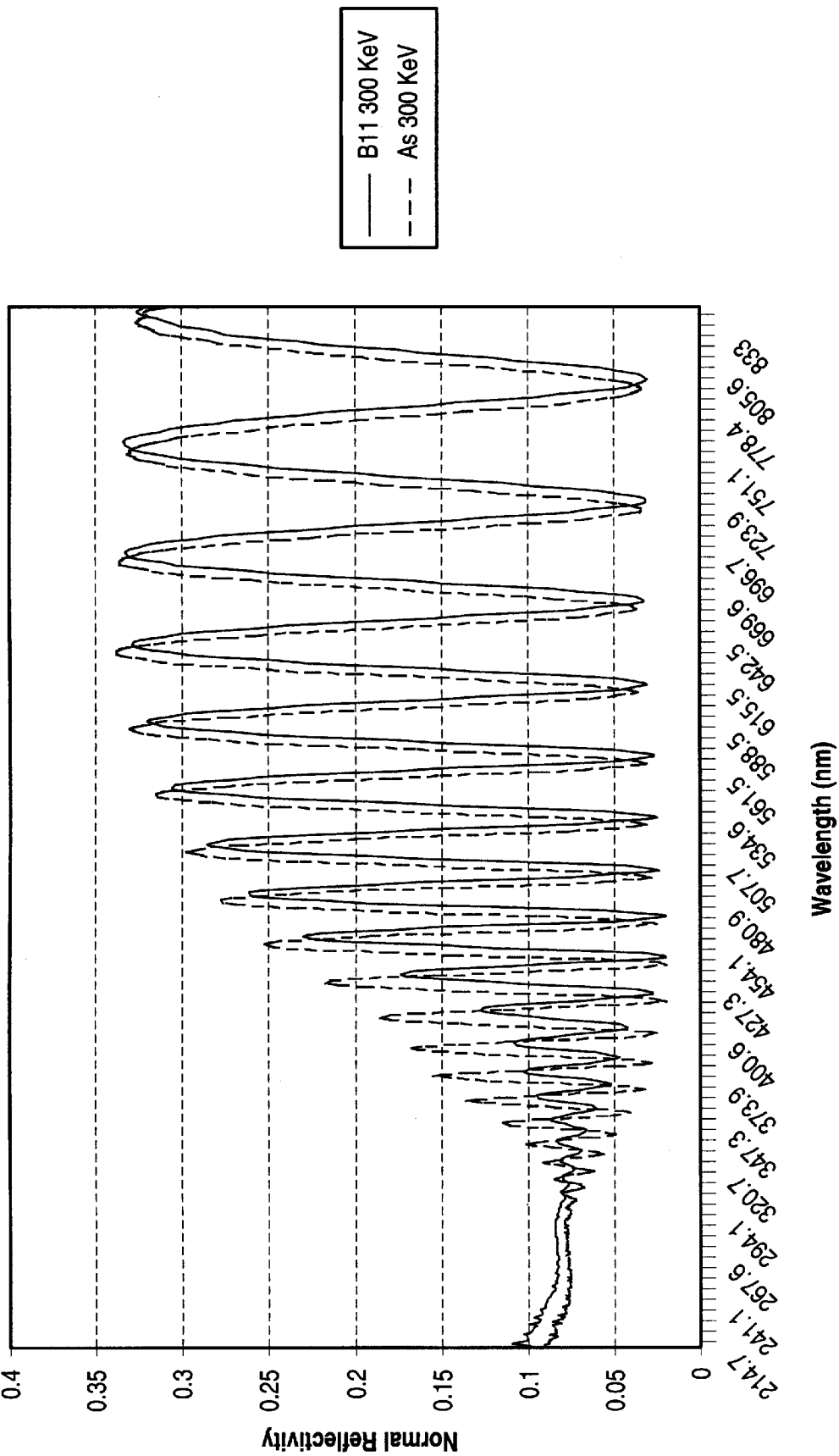
FIG. 5 depicts a plot of reflectance data versus wavelength for implantation of various dopant species at constant implant energy.
Figure 6:
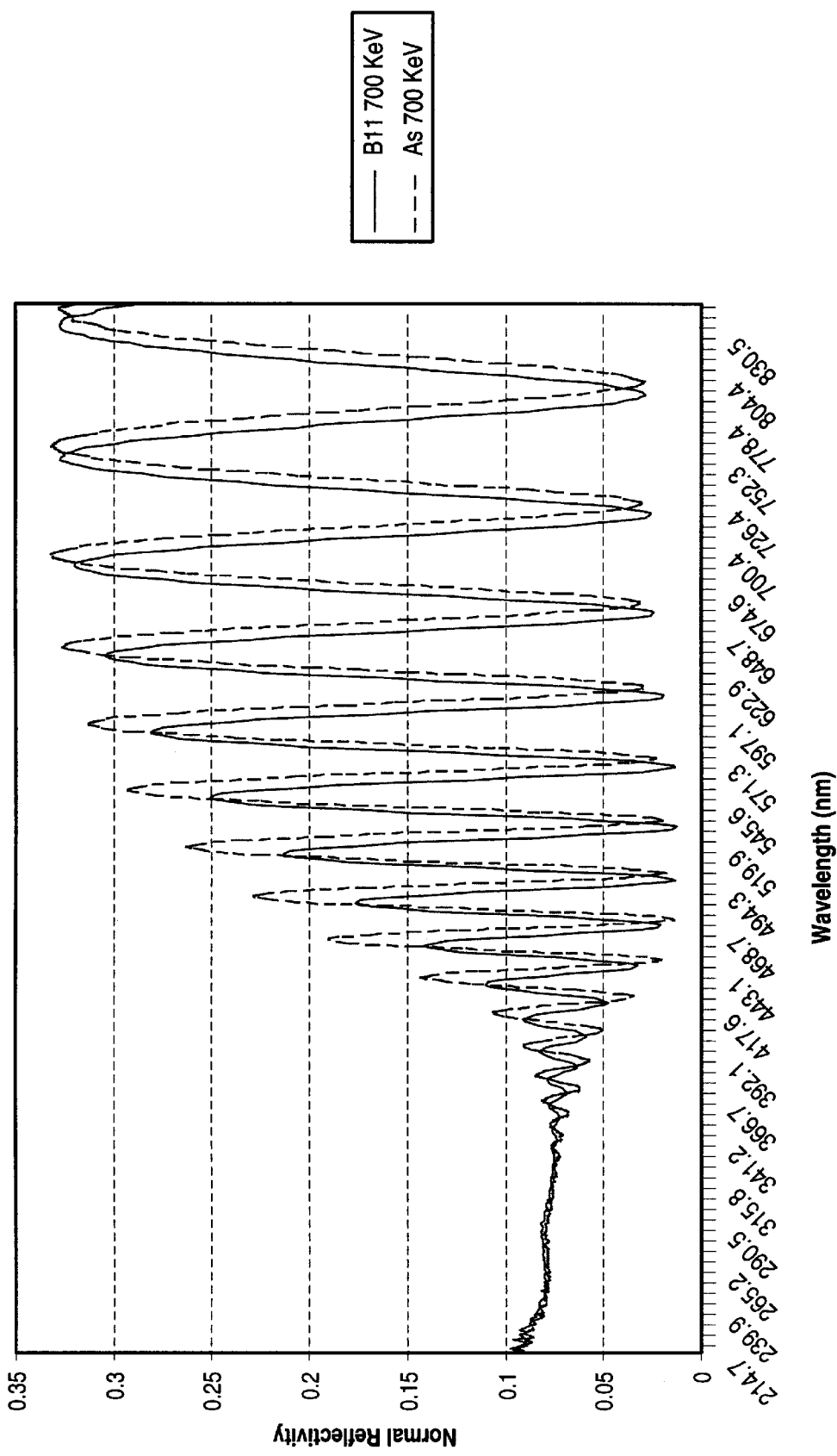
FIG. 6 depicts a plot of reflectance data versus wavelength for implantation of various dopant species at constant implant energy.

All other processing parameters were held constant in the above experiments, therefore, similarly prepared wafers were used to make comparisons of spectroscopic reflectance data for different dopant species. Therefore, the wafers, which were implanted at constant energy, may also be used to analyze the effects of arsenic and boron implanted on the optical properties of the resist. As shown in FIG. 5, the reflectance data for resist implanted with boron and arsenic at a lower implant energy of 300 KeV was compared. The plot shows the largest variations in frequency and amplitude in a range of wavelengths of approximately 320 nm to approximately 500 nm. A similar comparison of the reflectance data for resist implanted with boron and arsenic at a higher implant energy of 700 KeV was also compared. Implanting with different dopant species at this implant energy appears to cause little offset in the frequency of the reflectance data across the entire spectrum of wavelengths. Using different dopant species at the higher implant energy, however, appears to cause an offset in the amplitude of the two sets of data. Therefore, the largest variations in the amplitude of the data were observed in the wavelength region of approximately 450 nm to approximately 600 nm. The larger variations of the amplitude of the reflectance data indicate that the resist exhibits increased sensitivity in this wavelength range. Optical modeling was then performed as described above.

Figure 7:
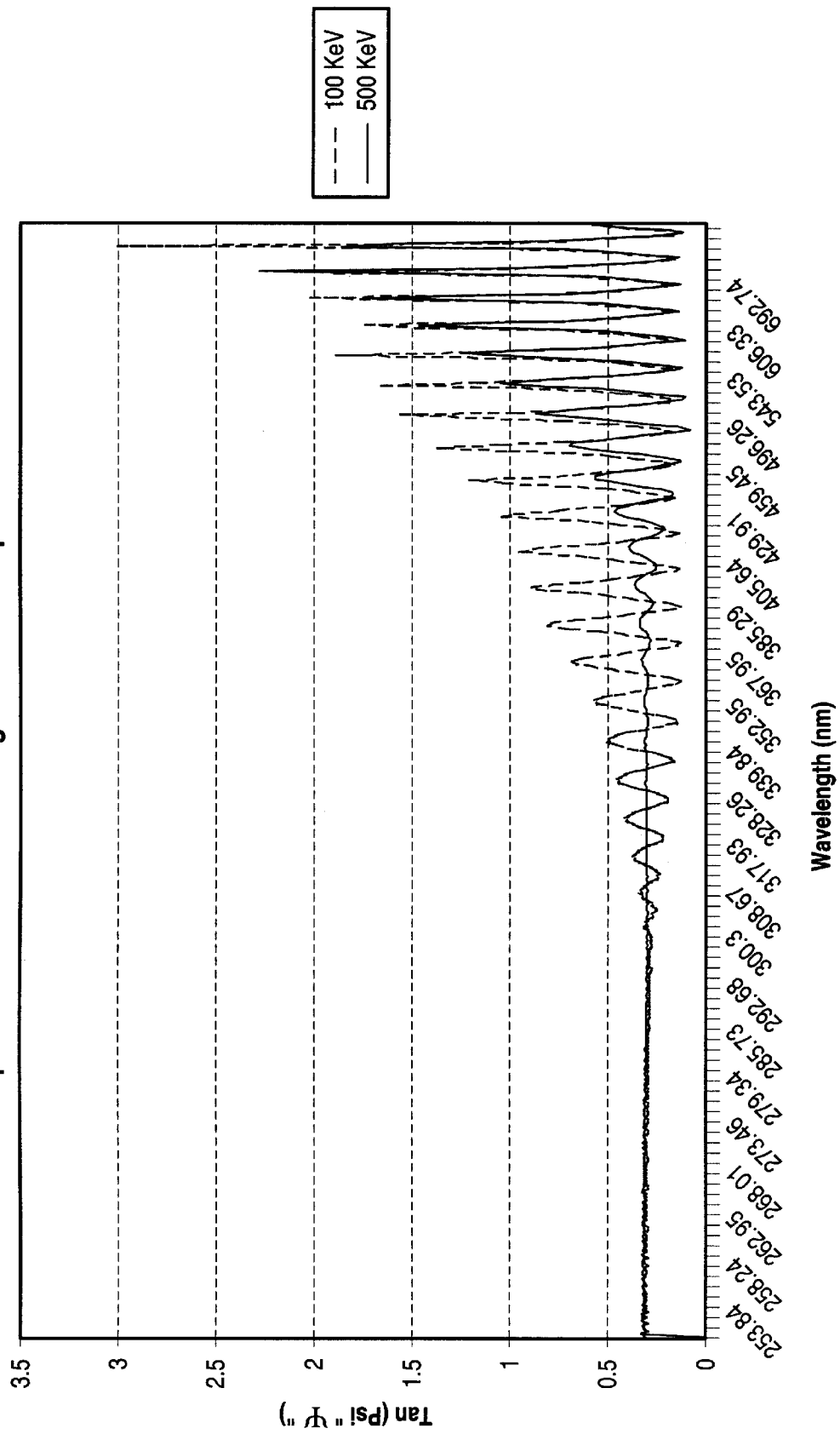
FIG. 7 depicts a plot of ellipsometric data versus wavelength at various implant energies for a boron implantation process.
Figure 8:
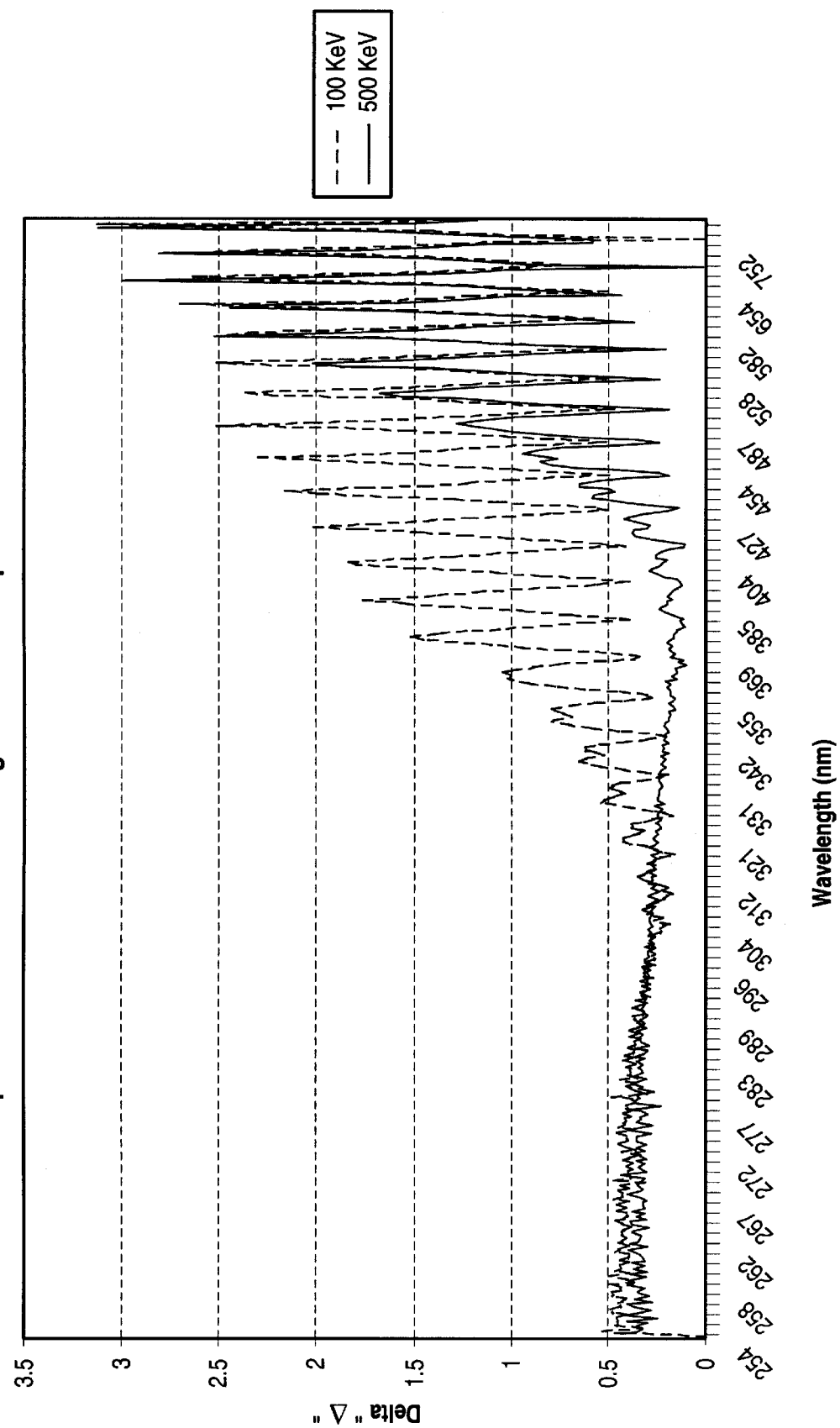
FIG. 8 depicts a plot of ellipsometric data versus wavelength at various implant energies for a boron implantation process.

The wafers which were subjected to arsenic and boron implantation were also examined using a spectroscopic ellipsometer integrated into the UV1280 tool from KLA-Tencor Corporation, San Jose, Calif. Ellipsometric data that was collected for the wafers that were implanted with boron is shown in FIGS. 7 and 8. The ellipsometric parameters are shown as tan ψ and Δ. This data was generated using a personal computer with appropriate software capability to perform iterative data-fitting calculations. For example, the software capability integrated into the UV1280 tool was used to convert the measured data from a detector of the spectroscopic ellipsometer to the ellipsometric parameters ψ and Δ.

It will be appreciated to those skilled in the art having the benefit of this disclosure that this invention is believed to provide a method to monitor the process conditions of a semiconductor manufacturing process, such as ion implantation, by measuring the optical properties of a masking material. Further modifications and alternative embodiments of various aspects of the invention will be apparent to those skilled in the art in view of this description. For example, the process control method may also be used to monitor and evaluate any process which uses a masking material, such as etch processes. In addition, the process control method may also include alternative techniques to determine the optical properties of the materials, such as beam profile ellipsometry or deep ultra violet reflective spectrometry. It is intended that the following claims be interpreted to embrace all such modifications and changes and, accordingly, the specification and drawings are to be regarded in an illustrative rather than a restrictive sense.

What is claimed is:

1. A method for evaluating an ion implantation process, comprising:

forming a masking material upon a semiconductor substrate;

implanting ions into the masking material, wherein the implantation of ions into the masking material alters an optical property of the masking material;

measuring at least one optical property of the masking material using a broadband radiation technique to measure a property of light reflected from the masking material and the semiconductor substrate; and determining at least one characteristic of the implanted ions in the masking material, wherein the characteristic is a function of the measured optical property of the masking material.

2. The method of claim 1, wherein the characteristic comprises an implantation energy of the ions when the ions are implanted into the masking material.

3. The method of claim 1, wherein the characteristic comprises a species of the implanted ions in the masking material.

4. The method of claim 1, wherein the characteristic comprises a concentration of the implanted ions in the masking material.

5. The method of claim 1, wherein the characteristic comprises a presence of implanted ions in the masking material.

6. The method of claim 1, further comprising determining at least two characteristics of the implanted ions in the masking material, wherein the characteristic comprises an implantation energy of the ions when the ions are implanted into the masking material, a species, a concentration or a presence of the implanted ions in the masking material.

7. The method of claim 6, wherein determining at least two characteristics is performed substantially simultaneously.

8. The method of claim 1, further comprising determining at least one characteristic of implanted ions in a portion of a semiconductor substrate, wherein the characteristic of the implanted ions in the portion of the semiconductor substrate is a function of the measured optical property of the masking material.

9. The method of claim 8, wherein the characteristic of implanted ions in the portion of the semiconductor substrate comprises a concentration of the implanted ions in the portion of the semiconductor substrate.

10. The method of claim 8, wherein the characteristic of implanted ions in the portion of the semiconductor substrate comprises a depth of the implanted ions in the portion of the semiconductor substrate.

11. The method of claim 8, wherein the characteristic of implanted ions in the portion of the semiconductor substrate comprises a dose of the ions when the ions are implanted into the portion of the semiconductor substrate.

12. The method of claim 8, wherein the characteristic of implanted ions in the portion of the semiconductor substrate comprises an energy of the ions when the ions are implanted into the portion of the semiconductor substrate.

13. The method of claim 8, wherein the characteristic of implanted ions in the portion of the semiconductor substrate comprises a distribution of the implanted ions in the portion of the semiconductor substrate, wherein the distribution of implanted ions is a function of a thickness of the implanted portion of the semiconductor substrate.

14. The method of claim 1, wherein the property of the light comprises polarization or intensity.

15. The method of claim 1, wherein the broadband radiation technique comprises spectroscopic ellipsometry.

16. The method of claim 1, wherein the broadband radiation technique comprises spectroscopic reflectometry.

17. The method of claim 1, wherein measuring the optical property of the masking material comprises measuring an index of refraction of the masking material.

18. The method of claim 1, wherein measuring the optical property of the masking material comprises measuring an extinction coefficient of the masking material.

19. The method of claim 1, wherein measuring the optical property of the masking material comprises measuring a thickness of the masking material.

20. The method of claim 1, further comprising measuring at least two optical properties of the masking material, wherein the optical properties of the masking material comprise thickness, index of refraction, or extinction coefficient of the masking material.

21. The method of claim 20, wherein measuring at least two optical properties of the masking material is performed substantially simultaneously.

22. The method of claim 1, wherein implanting ions into the masking material and measuring the optical property of the masking material are performed substantially simultaneously.

23. The method of claim 22, wherein the broadband radiation technique comprises using a spectroscopic device, and wherein the spectroscopic device is coupled to an ion implanter used to implant ions into the masking material.

24. The method of claim 23, wherein the spectroscopic device comprises a spectroscopic ellipsometer.

25. The method of claim 23, wherein the spectroscopic device comprises a spectroscopic reflectometer.

26. The method of claim 23, further comprising measuring the optical property of the masking material at predetermined time intervals during the implantation of ions into the masking material.

27. The method of claim 26, wherein a signature characterizing the implantation of ions into the masking material is obtained, and wherein the signature comprises at least one singularity representative of an end of implantation.

28. The method of claim 1, wherein the masking material comprises resist material.

29. The method of claim 1, wherein the masking material comprises silicon dioxide, silicon nitride, titanium nitride, or polycrystalline silicon.

30. The method of claim 1, wherein the masking material comprises a resist material disposed upon an inorganic masking material.

31. The method of claim 1, wherein the masking material substantially inhibits the implantation of ions into the semiconductor substrate.

32. The method of claim 1, wherein the ion implanted masking material comprises an upper portion, a middle portion and a lower portion, and wherein the upper portion comprises a physically damaged layer, and wherein the implanted ions are substantially disposed within the middle portion, and wherein the lower portion is substantially free of ions.

33. The method of claim 32, wherein determining a characteristic of the implanted ions in the masking material comprises determining a thickness of the upper portion of the ion implanted masking material.

34. The method of claim 32, wherein determining a characteristic of the implanted ions in the masking material comprises determining a thickness of the middle portion of the ion implanted masking material.

35. The method of claim 32, wherein determining a characteristic of the implanted ions in the masking material comprises determining a thickness of the lower portion of the ion implanted masking material.

36. The method of claim 32, wherein determining a characteristic of the implanted ions in the masking material comprises determining a thickness of at least two portions of the ion implanted masking material.

37. The method of claim 1, further comprising measuring the optical property of the masking material prior to the implantation of ions into the masking material.

38. The method of claim 37, further comprising comparing the optical property of the masking material prior to implantation to the optical property of the masking material subsequent to implantation, wherein the characteristic of the implanted ions comprises a presence of ions in the masking material.

39. The method of claim 1, further comprising implanting ions into a portion of the semiconductor substrate, wherein the implantation of ions into the portion of the semiconductor substrate alters an optical property of the portion of the semiconductor substrate.

40. The method of claim 39, further comprising removing portions of the masking material to expose regions of the semiconductor substrate, and wherein implanting ions into a portion of the semiconductor substrate comprises implanting ions into exposed regions of the semiconductor substrate.

41. The method of claim 39, further comprising measuring an optical property of the portion of the semiconductor substrate and determining a characteristic of the implanted ions in the portion of the semiconductor substrate, wherein the characteristic comprises a function of the measured optical property of the portion of the semiconductor substrate.

42. The method of claim 41, wherein measuring the optical property of the masking material and measuring the optical property of the portion of the semiconductor substrate are performed substantially simultaneously.

43. The method of claim 41, wherein the characteristic comprises an implantation energy of the ions when the ions are implanted into the portion of the semiconductor substrate.

44. The method of claim 41, wherein the characteristic comprises a species of the implanted ions in the portion of the semiconductor substrate.

45. The method of claim 41, wherein the characteristic comprises a concentration of the implanted ions in the portion of the semiconductor substrate.

46. The method of claim 41, wherein the characteristic comprises a presence of the implanted ions in the portion of the semiconductor substrate.

47. The method of claim 41, wherein the characteristic comprises a depth of the implanted ions in the portion of the semiconductor substrate.

48. The method of claim 41, wherein the characteristic comprises a dose of the implanted ions when the ions are implanted in the portion of the semiconductor substrate.

49. The method of claim 41, wherein the characteristic comprises a distribution of the implanted ions in the portion of the semiconductor substrate.

50. The method of claim 41, wherein the characteristic of the implanted ions in the portion of the semiconductor substrate comprises an implantation energy of the ions when the ions are implanted into the semiconductor substrate, a species of the implanted ions, a concentration of the implanted ions, a presence of the implanted ions, a depth of the implanted ions, a dose of the implanted ions when the ions are implanted, or a distribution of the implanted ions in the portion of the semiconductor substrate.

51. The method of claim 41, wherein measuring the optical property of the portion of the semiconductor substrate comprises using a broadband radiation technique.

52. The method of claim 41, wherein implanting ions into a portion of the semiconductor substrate and measuring the optical property of the portion of the semiconductor substrate are performed substantially simultaneously.

53. The method of claim 52, wherein measuring the optical property of the portion of the semiconductor substrate comprises using a spectroscopic ellipsometer, and wherein the spectroscopic ellipsometer is coupled to an ion implanter.

54. The method of claim 52, wherein measuring the optical property of the portion of the semiconductor substrate comprises using a spectroscopic reflectometer, and wherein the spectroscopic reflectometer is coupled to an ion implanter.

55. The method of claim 54, further comprising measuring variations in the optical property of the portion of the semiconductor substrate during the implantation of ions into the portion of the semiconductor substrate.

56. The method of claim 55, further comprising obtaining a signature characterizing the implantation of ions into the portion of the semiconductor substrate, and wherein the signature comprises at least one singularity representative of an end of implantation.

57. The method of claim 41, wherein measuring the optical property of the portion of the semiconductor substrate comprises measuring an index of refraction of the portion of the semiconductor substrate.

58. The method of claim 41, wherein measuring the optical property of the portion of the semiconductor substrate comprises measuring an extinction coefficient of the portion of the semiconductor substrate.

59. The method of claim 41, wherein measuring the optical property of the portion of the semiconductor substrate comprises measuring a thickness of the portion of the semiconductor substrate.

60. The method of claim 41, wherein measuring the optical property of the portion of the semiconductor substrate comprises simultaneously measuring at least two optical properties of the portion of the semiconductor substrate, wherein the optical properties comprise thickness, index of refraction, or extinction coefficient of the portion of the semiconductor substrate.

61. The method of claim 41, further comprising measuring the optical property of the portion of the semiconductor substrate prior to implantation of ions into the portion of the semiconductor substrate.

62. The method of claim 61, further comprising comparing the optical property of the portion of the semiconductor substrate prior to implantation and the optical property of the portion of the semiconductor substrate subsequent to implantation.

63. The method of claim 1, further comprising generating a set of data, the set of data comprising the measured optical properties of the masking material and the determined characteristic of the implanted ions in the masking material.

64. The method of claim 63, further comprising generating at least two sets of data, wherein the sets of data comprise data generated using at least two different devices, and wherein the devices are configured to measure the optical property of the masking material and to determine the characteristic of the implanted ions in the masking material.

65. The method of claim 63, further comprising using the set of data to calibrate additional devices.

66. The method of claim 63, further comprising using the set of data to monitor the performance of additional devices.

67. A computer-implemented method for controlling an optical inspection device, comprising:
  controlling the optical inspection device to measure an optical property of an ion implanted masking material by using a broadband radiation technique to measure a property of light reflected from the masking material and the semiconductor substrate, wherein the ion implanted masking material is formed by implanting ions into a masking material residing upon a semiconductor substrate, and wherein the implantation of ions into the masking material alters an optical property of the masking material; and
  determining at least one characteristic of the implanted ions in the masking material, wherein the characteristic comprises a function of the measured optical property of the ion implanted masking material.

68. A system configured to monitor and evaluate an ion implantation process, comprising:
  an ion implanter configured produce and direct ions toward a wafer during use; and
  a spectroscopic device coupled to the ion implanter, wherein the spectroscopic device is configured to measure at least one optical property of the wafer during use by using a broadband radiation technique to measure a property of light reflected from the wafer, and wherein implantation of ions into the wafer alters an optical property of the wafer.

69. A system for inspecting a wafer, comprising:

a spectroscopic device configured to measure at least one optical property of a wafer during use;

an operating system configured to determine at least one characteristic of the implanted ions in the wafer during use, wherein the characteristic comprises a function of the measured optical property of the wafer; and a dual-beam device configured to measure a thickness of the wafer during use, and wherein the operating system is coupled to the spectroscopic device and the dual-beam device.

70. A method of fabricating a semiconductor device, comprising:

implanting ions into a wafer, the wafer comprising a masking material and a semiconductor substrate, wherein the masking material is arranged on at least a portion of the semiconductor substrate, and wherein at least a portion of the ions are implanted into the masking material, and wherein the implantation of ions into the masking material alters an optical property of the masking material;

measuring at least one optical property of the masking material by using a broadband radiation technique to measure a property of light reflected from the masking material and the semiconductor substrate; and determining at least one characteristic of the implanted ions in the masking material, wherein the characteristic comprises a function of the measured optical property of the masking material.

* * * * *